US012217856B2

(12) United States Patent
Perugupalli et al.

(10) Patent No.: US 12,217,856 B2
(45) Date of Patent: Feb. 4, 2025

(54) APPARATUS AND METHOD FOR IDENTIFYING REGIONS OF INTEREST DURING SLIDE DIGITIZATION

(71) Applicant: Pramana, Inc., Cambridge, MA (US)

(72) Inventors: Prasanth Perugupalli, Cary, NC (US); Jaya Jain, Shahpura (IN); Durgaprasad Dodle, Telangana (IN); Prateek Jain, Karnataka (IN); Suhash Gerald, Karnataka (IN); Dipankar Das, Bangalore (IN)

(73) Assignee: Pramana, Inc., Cambridge, MA (US)

( * ) Notice: Subject to any disclaimer, the term of this patent is extended or adjusted under 35 U.S.C. 154(b) by 0 days.

(21) Appl. No.: 18/602,776

(22) Filed: Mar. 12, 2024

(65) Prior Publication Data

US 2024/0371501 A1   Nov. 7, 2024

Related U.S. Application Data

(60) Provisional application No. 63/463,668, filed on May 3, 2023.

(51) Int. Cl.
*G16H 30/40* (2018.01)
*G16H 50/20* (2018.01)
*G16H 70/60* (2018.01)

(52) U.S. Cl.
CPC ............. *G16H 30/40* (2018.01); *G16H 50/20* (2018.01); *G16H 70/60* (2018.01)

(58) Field of Classification Search
CPC ......... G16H 30/40; G16H 50/20; G16H 70/60
See application file for complete search history.

(56) References Cited

U.S. PATENT DOCUMENTS 7,343,033 B2   3/2008   Bartels
7,949,167 B2   5/2011   Krishnan et al.
(Continued)

FOREIGN PATENT DOCUMENTS

WO   WO-2019199392 A1 * 10/2019   .......... G02B 21/367
WO   2023211411 A1   11/2023

OTHER PUBLICATIONS

Ghosh Pramit et al: "Passive Auto Focusing of Pathological Microscope with Intelligent Field Image Collection Mechanism", Journal of Medical Systems, [Online] vol. 45, No. 2, Jan. 16, 2021 (Jan. 16, 2021), XP093200766, New York ISSN: 0148-5598, DOI: 10.1007/s10916-020-01688-2 Retrieved from the Internet: URL: http://link.springer.com/article/10.1007/s10916-020-01688-2/fulltext.html> [retrieved on 2024-09-03].

(Continued)

*Primary Examiner* — Robert A Sorey
*Assistant Examiner* — Kimberly A. Sass
(74) *Attorney, Agent, or Firm* — Caldwell Intellectual Property Law

(57) ABSTRACT

An apparatus for identifying regions of interest during slide digitization is disclosed. The apparatus includes at least processor and a memory communicatively connected to the processor. The memory contains instructions configuring the processor to receive a user dataset associated with at least a pathology slide. The memory contains instructions configuring the processor to identify one or more regions of interest within at least a pathology slide as a function of the user dataset. The memory contains instructions configuring the processor to identify at least one scan parameter as a function of the one or more regions of interest. The memory contains instructions configuring the processor to generate a digitized slide by scanning the at least a pathology slide as a function the at least one scan parameter.

18 Claims, 10 Drawing Sheets

(56) References Cited

U.S. PATENT DOCUMENTS

| | | | |
|---|---|---|---|
| 11,594,024 B2* | 2/2023 | Stumpe | G06T 11/60 |
| 2022/0261988 A1 | 8/2022 | Yoo et al. | |
| 2023/0068571 A1* | 3/2023 | Linhart | G02B 21/367 |

OTHER PUBLICATIONS

Bandi Peter et al: "Resolution-agnostic tissue segmentation in whole-slide histopathology images with convolutional neural networks", PEERJ, [Online] vol. 7, Dec. 17, 2019 (Dec. 17, 2019), page e8242, XP093140917, ISSN: 2167-8359, DOI: 10.7717/peerj.8242 Retrieved from the Internet: URL:https://peerj.com/articles/8242.html> [retrieved on Mar. 9, 2024].

Zarella Mark D et al: "High-throughput whole-slide scanning to enable large-scale data repository building", The Journal of Pathology, [Online] vol. 257, No. 4, Jun. 8, 2022 (Jun. 8, 2022), pp. 383-390, XP093200746, Hoboken, USA ISSN: 0022-3417, DOI: 10.1002/path.5923 Retrieved from the Internet: URL:https://onlinelibrary.wiley.com/doi/full-XML/10.1002/path.5923> [retrieved on Mar. 9, 2024].

Jiang Shaowei et al: "Transform-and multi-domain deep learning for single-frame rapid autofocusing in whole slide imaging", Biomedical Optics Express, vol. 9, No. 4, Apr. 1, 2018 (Apr. 1, 2018), p. 1601, XP055880882, United States ISSN: 2156-7085, DOI: 10.1364/BOE.9.001601.

Rai Dastidar Tathagato et al: "Whole slide imaging system using deep learning-based automated focusing", Biomedical Optics Express, vol. 11, No. 1, Dec. 23, 2019 (Dec. 23, 2019), p. 480, XP055917112, United States ISSN: 2156-7085, DOI: 10.1364/BOE.379780.

European Search Report; EP 24 17 3943; Sep. 3, 2024; By: Examiner Meier Ueli.

\* cited by examiner

APPARATUS AND METHOD FOR IDENTIFYING REGIONS OF INTEREST DURING SLIDE DIGITIZATION

CROSS-REFERENCE TO RELATED APPLICATIONS

This application claims the benefit of priority of U.S. Provisional Patent Application Ser. No. 63/463,668, filed on May 3, 2023, and titled "SYSTEMS AND METHODS FOR DETECTION OF PATHOLOGICAL FEATURES DURING SLIDE DIGITIZATION," which is incorporated by reference herein in its entirety.

FIELD OF THE INVENTION

The present invention generally relates to the field of automated slide digitization. In particular, the present invention is directed to an apparatus and a method for identifying regions of interest during slide digitization.

BACKGROUND

Examination of slides containing biomedical specimens, such as tissue samples, under a microscope provides data that can be exploited for a variety of biomedical applications. For example, physicians or other qualified individuals may be able to diagnose pathological conditions or detect microbial organisms. It is desirable to digitize microscope slides for downstream analysis. Slide digitization offers opportunities for healthcare providers to provide enhanced patient care in a faster and more efficient manner. Additionally, slide digitization is beneficial in clinical and academic contexts.

SUMMARY OF THE DISCLOSURE

In an aspect, an apparatus for identifying regions of interest during slide digitization is disclosed. The apparatus includes at least processor and a memory communicatively connected to the processor. The memory contains instructions configuring the processor to receive a user dataset associated with at least a pathology slide. The memory contains instructions configuring the processor to identify one or more regions of interest within at least a pathology slide as a function of the user dataset. The memory contains instructions configuring the processor to identify at least one scan parameter as a function of the one or more regions of interest. The memory contains instructions configuring the processor to generate a digitized slide by scanning the at least a pathology slide as a function the at least one scan parameter. The memory contains instructions configuring the processor to display the digitized slide using a user interface at a display device.

In another aspect, a method for the identifying regions of interest during slide digitization is disclosed. The method includes receiving, using at least a processor, a user dataset associated with at least a pathology slide. The method includes identifying, using the at least a processor, one or more regions of interest within at least a pathology slide as a function of the user dataset. The method includes identifying, using the at least a processor, at least one scan parameter as a function of the one or more regions of interest. The method includes generating, using the at least a processor, a digitized slide by scanning the at least a pathology slide as a function the at least one scan parameter. The method includes displaying, using a user interface at a display device, the digitized slide.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations, and fragmentary views. In certain instances, details that are not necessary for an understanding of the embodiments or that render other details difficult to perceive may have been omitted.

DETAILED DESCRIPTION

At a high level, aspects of the present disclosure are directed to an apparatus and a method for identifying regions of interest during slide digitization. The apparatus includes at least processor and a memory communicatively connected to the processor. The memory contains instructions configuring the processor to receive a user dataset associated with at least a pathology slide. The memory contains instructions configuring the processor to identify one or more regions of interest within at least a pathology slide as a function of the user dataset. The memory contains instructions configuring the processor to identify at least one scan parameter as a function of the one or more regions of interest. The memory contains instructions configuring the processor to generate a digitized slide by scanning the at least a pathology slide as a function the at least one scan parameter and display the generated digitized slide using a user interface at a display device. Exemplary embodiments illustrating aspects of the present disclosure are described below in the context of several specific examples.

Figure 1:
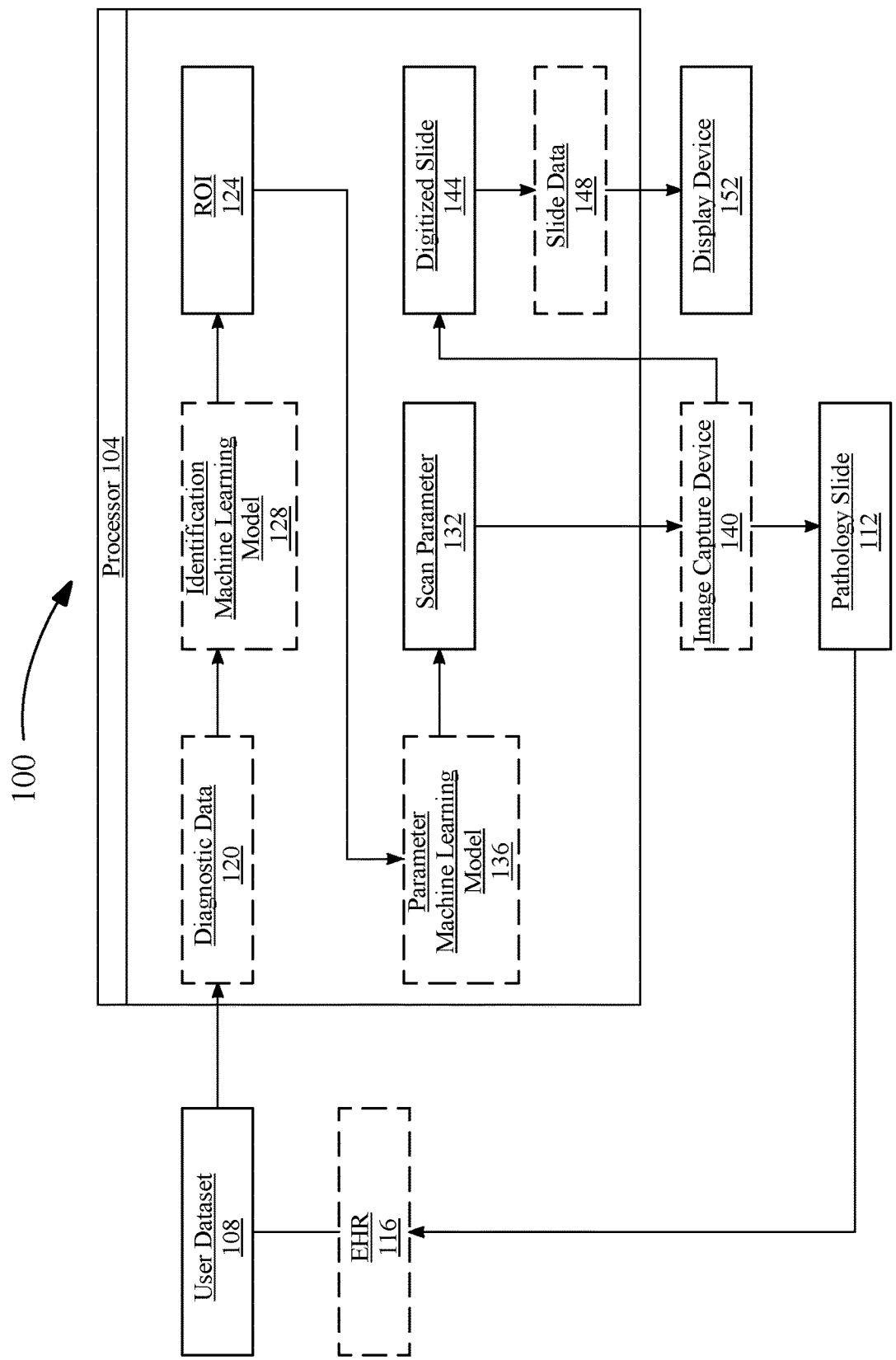
FIG. 1 is a block diagram of an exemplary embodiment of an apparatus for identifying regions of interest during slide digitization.

Referring now to FIG. 1, an exemplary embodiment of an apparatus 100 for identifying regions of interest during slide digitization is illustrated. Apparatus 100 includes a processor 104. Processor 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Processor 104 may include a single computing device operating independently, or may include two or more computing device operating in concert, in parallel, sequentially or the like; two or more computing devices may be included together in a single computing device or in two or more computing devices. Processor 104 may interface or communicate with one or more additional devices as described below in further detail via a network interface device. Network interface device may be utilized for connecting processor 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Processor 104 may include but is not limited to, for example, a computing device or cluster of computing devices in a first location and a second computing device or cluster of computing devices in a second location. Processor 104 may include one or more computing devices dedicated to data storage, security, distribution of traffic for load balancing, and the like. Processor 104 may distribute one or more computing tasks as described below across a plurality of computing devices of computing device, which may operate in parallel, in series, redundantly, or in any other manner used for distribution of tasks or memory between computing devices. Processor 104 may be implemented using a "shared nothing" architecture in which data is cached at the worker, in an embodiment, this may enable scalability of apparatus 100 and/or computing device.

With continued reference to FIG. 1, processor 104 may be designed and/or configured to perform any method, method step, or sequence of method steps in any embodiment described in this disclosure, in any order and with any degree of repetition. For instance, processor 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Processor 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, apparatus 100 includes a memory. Memory is communicatively connected to processor 104. Memory may contain instructions configuring processor 104 to perform tasks disclosed in this disclosure. As used in this disclosure, "communicatively connected" means connected by way of a connection, attachment, or linkage between two or more relata which allows for reception and/or transmittance of information therebetween. For example, and without limitation, this connection may be wired or wireless, direct, or indirect, and between two or more components, circuits, devices, systems, apparatus, and the like, which allows for reception and/or transmittance of data and/or signal(s) therebetween. Data and/or signals therebetween may include, without limitation, electrical, electromagnetic, magnetic, video, audio, radio, and microwave data and/or signals, combinations thereof, and the like, among others. A communicative connection may be achieved, for example, and without limitation, through wired or wireless electronic, digital, or analog, communication, either directly or by way of one or more intervening devices or components. Further, communicative connection may include electrically coupling or connecting at least an output of one device, component, or circuit to at least an input of another device, component, or circuit. For example, without limitation, via a bus or other facility for intercommunication between elements of a computing device. Communicative connecting may also include indirect connections via, for example, and without limitation, wireless connection, radio communication, low power wide area network, optical communication, magnetic, capacitive, or optical coupling, and the like. In some instances, the terminology "communicatively coupled" may be used in place of communicatively connected in this disclosure.

With continued reference to FIG. 1, processor 104 may be configured to receive a user dataset 108. For the purposes of this disclosure, a "user dataset" is a representation of information and/or data describing information an individual or a group of patients. A user dataset 108 may be a structured collection of data that is organized and presented in a specific format for analysis and interpretation. It may consist of individual data points or observations, each representing a specific piece of information. A user dataset 108 can be generated through various means, including manual data entry, data collection from sensors or instruments, scraping data from websites, or extracting data from existing databases. A dataset may include a plurality of individual data points, often referred to as records, instances, or observations. Each data point represents a distinct unit of information, such as a customer, a transaction, a measurement, or any other relevant entity.

With continued reference to FIG. 1, a user dataset 108 may include a plurality textual data. As used in the current disclosure, "textual data" is a collection of data that consists of text-based information. Examples of textual data may include documents, captions, sentences, paragraphs, free-text fields, transcriptions, prognostic labels, and the like. In some embodiments, textual data within a first data set may be related to a pathology slide 112. As used in the current disclosure, a "pathology slide" is a glass slide containing a portion of biopsied biological material from a patient. A pathology slide 112 may include biopsied tissue from a patient, wherein the biopsied tissue is sliced into very thin layers and placed on a glass slide. A user dataset 108 may include a written description of various aspects of the pathology slide 112. A user dataset 108 may include documents surrounding the pathology slide 112. These documents may include information regarding testing, analysis, storage, staining, and disposal of pathology slides by medical professionals. The user dataset 108 may include information that describes and provides context for the pathology slide 112, enabling researchers, clinicians, or data analysts to understand and analyze the slide effectively. In a non-limiting example, the user dataset 108 may include a slide identifier, slide description, clinical information, pathology reports, annotations, notes, research findings, and the like. A user dataset 108 may include a brief description or summary of the pathology slide 112, providing an overview of its content, specimen type, and relevant characteristics. This description can include details such as tissue type, staining techniques used, and any specific features or abnormalities present in the slide. In other embodiments, the user dataset 108 may include a pathology report generated by a medical professional or data scientist after analyzing the slide. This report may provide detailed findings, observations, interpretations, and diagnoses based on the examination of the slide. It may include descriptions of tissue structures, cell morphology, tumor grading, staging, and other relevant pathological features.

With continued reference to FIG. 1, a user dataset 108 may include a plurality image data. As used in the current disclosure, "image data" is a collection of data that consists of data associated with one or more images. Image data may include an initial scan of the pathology slide 112 using an image capture device. The image data may include a low magnification or no magnification version of the pathology slide that provides overview of the tissue sample and its general condition. The image data may capture the general architecture of the tissue, including the layout of different tissue types, such as epithelial, connective, or muscular tissues. Image data may also include an image of the pathology slide that includes a photographic overview of the entire slide, including the label, slide identifier (i.e., Barcode, QR code, Identification Number, and the like), and the tissue section's placement on the slide. The user dataset 108 may also include a plurality of medical images. Medical images may include X-rays, CT scans, MRI, Ultrasound, PET scans, Electrocardiogram scans, and the like. In some cases, image data may include either 2D and/or 3D medical images. A user dataset 108 may be collection of multiple images organized and presented in a specific format for analysis, training machine learning models, or any other image-related tasks. It may consist of a diverse range of images captured from various sources, such as digital cameras, satellites, medical imaging devices, microscopes, or other image acquisition methods. The image data may be stored in a digital format, such as JPEG, PNG, or TIFF. Image data may include both color images and/or grayscale images. The term "image data" can be used interchangeably with "image," where "image" serves as a noun. An image may take various forms: it can be optical, for instance, created through the use of optics; material, like images captured on film; digital, such as those represented in bitmap format; or encompass any medium capable of depicting a physical scene, space, and/or object. Furthermore, when "image" is utilized as a verb in this document, it pertains to the process of creating and/or forming an image.

With continued reference to FIG. 1, user dataset 108 may include a plurality of metadata. As used in the current disclosure, "metadata" refers to descriptive information or attributes that provide context, structure, and meaning to data. Metadata is essentially data about data. Metadata helps in understanding and managing various aspects of data, such as its origin, content, format, quality, and usage. It plays a crucial role in organizing, searching, and interpreting data effectively. Metadata may include descriptive metadata, structural metadata, administrative metadata, technical metadata, provenance metadata, usage metadata, and the like. Metadata may be organized and managed through metadata schemas, standards, or frameworks. These provide guidelines and specifications for capturing, storing, and exchanging metadata in a consistent and structured manner. In some cases, metadata may be associated with textual data or image data. Metadata may also be associated with a pathology slide 112. Metadata may provide additional descriptive information or attributes that are linked to the image data or textual data associated with the pathology slide 112. Metadata associated with the plurality of datasets 108 may include patient information. Patient information may include data such as the patient's name, unique patient identifier (ID), age, gender, and any other relevant demographic information. Patient information helps in identifying and associating the slide with the correct individual's medical records. Metadata may also include case specific details, wherein case specific details may include information about the specific case or clinical scenario related to the slide. Case specific details may include information about the case number, referring physician, clinical history, relevant symptoms, or any other pertinent details that aid in understanding the context of the slide. In some cases, metadata may include information related to the specific specimen type of the slide. This may include the type of tissue or sample that the slide represents. Metadata may contain notes, comments, or observations made by the pathologist or other medical professional. These annotations might highlight specific features, anomalies, or noteworthy aspects of the slide that are important for interpretation or follow-up analysis. The date and time when the slide was prepared, analyzed, or labeled can be associated as metadata. This information helps in tracking and maintaining a chronological record of slide-related activities. It could be breast tissue, lung biopsy, skin lesion, or any other anatomical or pathological specimen. In some embodiments, metadata may contain information regarding staining or preparation technique, pathological diagnosis, and the like.

With continued reference to FIG. 1, processor 104 may be configured to receive a user dataset 108 from one or more electronic health records (EHR) 116. As used in the current disclosure, "electronic health record" is a data structure which includes a collection of a health data associated with the user. As used in the current disclosure, "health data" refers to the collection of information related to a patient's health and treatment history. Health data may include elements of data regarding treatment records, medical history, laboratory results, radiology reports, medical records, clinical notes, and the like. An electronic health record (EHR) 116 may be a digital version of a patient's medical information that is stored and managed in a computerized system. An EHR 116 may be a collection of a patient's health-related data that includes medical history, diagnoses, medications, treatment plans, test results, and other relevant health information. EHRs 116 may contain a wide range of patient information, including personal demographics, medical history, allergies, immunizations, medications, laboratory results, imaging reports, surgical procedures, and progress notes. This comprehensive data provides a complete overview of a patient's health and facilitates informed decision-making. EHRs 116 may include a patient's past and current medical conditions, surgeries, allergies, immunization records, medications, and any significant health events. EHRs 116 may additionally include a large amount of information regarding the patient's health background. This may include previous diagnosis, medical tests, medical imaging, and the like. EHRs 116 may include documentation, observations, assessments, and treatment plans from medical professionals. This may include progress notes, discharge summaries, and other relevant clinical documentation. EHRs may include information related to prescribed medications, including dosage, frequency, symptoms, effect, and duration. EHRs may include test results, which may include laboratory test results, radiology reports, medical imaging reports, and other diagnostic imaging findings. EHRs 116 may include a plurality of metadata 116, as mentioned herein above.

With continued reference to FIG. 1, EHRs 116 may be received by processor 104 via user input. For example, and without limitation, the user or a third party may manually input EHRs 116 using a graphical user interface of processor 104 or a remote device, such as for example, a smartphone or laptop. EHRs 116 may additionally be generated via the answer to a series of questions. In a non-limiting embodiment, a user may be prompted to input specific information or may fill out a questionnaire. In an embodiment, a graphical user interface may display a series of questions to prompt a user for information pertaining to the EHRs 116. The EHRs 116 may be transmitted to processor 104, such as via a wired or wireless communication, as previously discussed in this disclosure.

With continued reference to FIG. 1, the EHR 116 may include a plurality of multi-modal data associated with a user. As used in the current disclosure, "multi-modal data" is data which includes a plurality of modalities data. Modalities of data may include images, text, audio, documents, electronic health records, sensor data, and the like. Multi-modal data may include textual data. Textual data may include any written information, such as documents, emails, notes, handwriting, chat conversations, and the like. Examples of textual data may include documents, captions, sentences, paragraphs, free-text fields, transcriptions, prognostic labels, and the like. Textual data may include data from a plurality of digital or handwritten notes. Notes may be written by a medical professional. The notes may depict conditions of the patient. Textual data may be associated with electronic health records (EHRs). Textual data may refer to the written or typed information that is recorded and stored as part of a patient's health record in a digital format. It includes a wide range of textual information that provides details about the patient's medical history, diagnoses, treatments, procedures, medications, observations, clinical notes, and other relevant healthcare information. Multi-modal data may include image data. Image data may encompass visual representations captured through cameras or generated through medical imaging, graphs, microscopes, or other image capturing systems. Image data associated with electronic health records (EHRs) refers to the visual information that is linked or integrated with the patient's health record. It includes medical images such as X-rays, CT scans, MRI scans, ultrasound images, endoscopy images, pathology slides 112, and other types of diagnostic or clinical images.

Still referring to FIG. 1, processor 104 may use optical character recognition to generate a user dataset 108. Optical character recognition (OCR) may include automatic conversion of images of written (e.g., typed, handwritten or printed text) into machine-encoded text. Images of written or printed text may be included in image data, textual data, or any other data mentioned throughout this disclosure. In some cases, recognition of at least a keyword from an image component may include one or more processes, including without limitation optical character recognition (OCR), optical word recognition, intelligent character recognition, intelligent word recognition, and the like. In some cases, OCR may recognize written text, one glyph or character at a time. In some cases, optical word recognition may recognize written text, one word at a time, for example, for languages that use a space as a word divider. In some cases, intelligent character recognition (ICR) may recognize written text one glyph or character at a time, for instance by employing machine learning processes. In some cases, intelligent word recognition (IWR) may recognize written text, one word at a time, for instance by employing machine learning processes.

Still referring to FIG. 1, in some cases OCR may be an "offline" process, which analyses a static document or image frame. In some cases, handwriting movement analysis can be used as input to handwriting recognition. For example, instead of merely using shapes of glyphs and words, this technique may capture motions, such as the order in which segments are drawn, the direction, and the pattern of putting the pen down and lifting it. This additional information can make handwriting recognition more accurate. In some cases, this technology may be referred to as "online" character recognition, dynamic character recognition, real-time character recognition, and intelligent character recognition.

Still referring to FIG. 1, in some cases, OCR processes may employ pre-processing of image component. Pre-processing process may include without limitation de-skew, de-speckle, binarization, line removal, layout analysis or "zoning," line and word detection, script recognition, character isolation or "segmentation," and normalization. In some cases, a de-skew process may include applying a transform (e.g., homography or affine transform) to image component to align text. In some cases, a de-speckle process may include removing positive and negative spots and/or smoothing edges. In some cases, a binarization process may include converting an image from color or greyscale to black-and-white (i.e., a binary image). Binarization may be performed as a simple way of separating text (or any other desired image component) from a background of image component. In some cases, binarization may be required for example if an employed OCR algorithm only works on binary images. In some cases a line removal process may include removal of non-glyph or non-character imagery (e.g., boxes and lines). In some cases, a layout analysis or "zoning" process may identify columns, paragraphs, captions, and the like as distinct blocks. In some cases, a line and word detection process may establish a baseline for word and character shapes and separate words, if necessary. In some cases, a script recognition process may, for example in multilingual documents, identify script allowing an appropriate OCR algorithm to be selected. In some cases, a character isolation or "segmentation" process may separate signal characters, for example character-based OCR algorithms. In some cases, a normalization process may normalize aspect ratio and/or scale of image component.

Still referring to FIG. 1, in some embodiments an OCR process will include an OCR algorithm. Exemplary OCR algorithms include matrix matching process and/or feature extraction processes. Matrix matching may involve comparing an image to a stored glyph on a pixel-by-pixel basis. In some case, matrix matching may also be known as "pattern matching," "pattern recognition," and/or "image correlation." Matrix matching may rely on an input glyph being correctly isolated from the rest of the image component. Matrix matching may also rely on a stored glyph being in a similar font and at the same scale as input glyph. Matrix matching may work best with typewritten text.

Still referring to FIG. 1, in some embodiments, an OCR process may include a feature extraction process. In some cases, feature extraction may decompose a glyph into features. Exemplary non-limiting features may include corners, edges, lines, closed loops, line direction, line intersections, and the like. In some cases, feature extraction may reduce dimensionality of representation and may make the recognition process computationally more efficient. In some cases, extracted feature may be compared with an abstract vector-like representation of a character, which might reduce to one or more glyph prototypes. General techniques of feature detection in computer vision are applicable to this type of OCR. In some embodiments, machine-learning processes like nearest neighbor classifiers (e.g., k-nearest neighbors algorithm) can be used to compare image features with stored glyph features and choose a nearest match. OCR may employ any machine-learning process described in this disclosure, for example machine-learning processes described with reference to FIGS. 2 and 4-5. Exemplary non-limiting OCR software includes Cuneiform and Tesseract. Cuneiform is a multi-language, open-source optical character recognition system originally developed by Cognitive Technologies of Moscow, Russia. Tesseract is free OCR software originally developed by Hewlett-Packard of Palo Alto, California, United States.

Still referring to FIG. 1, in some cases, OCR may employ a two-pass approach to character recognition. Second pass may include adaptive recognition and use letter shapes recognized with high confidence on a first pass to recognize better remaining letters on the second pass. In some cases, two-pass approach may be advantageous for unusual fonts or low-quality image components where visual verbal content may be distorted. Another exemplary OCR software tool include OCRopus. OCRopus development is led by German Research Centre for Artificial Intelligence in Kaiserslautern, Germany. In some cases, OCR software may employ neural networks, for example neural networks as taught in reference to FIGS. 2 and 4-5.

Still referring to FIG. 1, in some cases, OCR may include post-processing. For example, OCR accuracy can be increased, in some cases, if output is constrained by a lexicon. A lexicon may include a list or set of words that are allowed to occur in a document. In some cases, a lexicon may include, for instance, all the words in the English language, or a more technical lexicon for a specific field. In some cases, an output stream may be a plain text stream or file of characters. In some cases, an OCR process may preserve an original layout of visual verbal content. In some cases, near-neighbor analysis can make use of co-occurrence frequencies to correct errors, by noting that certain words are often seen together. For example, "Washington, D.C." is generally far more common in English than "Washington DOC." In some cases, an OCR process may make us of a priori knowledge of grammar for a language being recognized. For example, grammar rules may be used to help determine if a word is likely to be a verb or a noun. Distance conceptualization may be employed for recognition and classification. For example, a Levenshtein distance algorithm may be used in OCR post-processing to further optimize results.

With continued reference to FIG. 1, processor 104 is configured to identify diagnostic data 120 from the user dataset 108. As used in the current disclosure, "diagnostic data" refers to information pertinent to the diagnosis and/or prognosis of a user's medical condition or health issue. This identification may be based on an analysis of data collected from the user dataset 108 and electronic health records (EHRs) 116. Diagnostic data 120 can pinpoint the specific condition or disease afflicting the user by leveraging known symptoms and conditions detailed within the user's health records or user dataset 108. Diagnostic data 120 may be used to identify a wide range of conditions that can be diagnosed, studied, and understood through the examination of pathology slides. This may include conditions such as cancer, infectious diseases, inflammatory diseases, degenerative diseases, cardiovascular diseases, kidney diseases, liver diseases, endocrine diseases, hematologic conditions, skin diseases, reproductive system diseases, gastrointestinal diseases, respiratory diseases, and the like. For instance, a user exhibiting symptoms such as chest pain, coughing up blood, a history of chronic smoking, dysphagia, and shortness of breath could be diagnosed with lung cancer after processor 104 analyzes associated medical images. In some instances, diagnostic data 120 could already be present within user dataset 108. Processors 104 may identify and extract crucial features or attributes from the dataset to formulate diagnostic data. These features encompass specific symptoms, test results, demographic details, and other relevant data points. The process of feature extraction involves transforming symptom-related information from unstructured data into structured, quantifiable features conducive for analysis by processor 104. It also includes selecting and transforming pertinent information (features) from raw data into formats that are informative for predictive modeling, pattern recognition, or any other data-driven tasks.

With continued reference to FIG. 1, processor 104 may employ specialized medical ontologies and dictionaries, such as SNOMED CT (Systematized Nomenclature of Medicine-Clinical Terms) or UMLS (Unified Medical Language System), to map symptom-related terms to standardized medical concepts, ensuring consistency and interoperability of extracted features from the user dataset 108. By analyzing the context in which symptoms are mentioned in user dataset 108, processor 104 may extract a semantic meaning, including understanding negations, co-occurrences, and modifiers which are essential for accurate feature extraction. Quantifying the frequency and severity of symptoms through descriptors like "frequent," "occasional," or "severe" and assigning numerical values or ordinal scales to these aspects permits a quantitative analysis. Moreover, processor 104 may extract temporal information concerning symptoms, including duration, onset dates, and symptom occurrence patterns, to further refine the diagnostic process.

With continued reference to FIG. 1, processor 104 may also groups related symptoms into clusters or categories based on their characteristics and related medical concepts through clustering, which simplifies the feature space and organizes symptoms for more effective analysis. For example, if the user dataset 108 indicates symptoms like cough, fever, and chest pain, processor 104 may classify these under lower respiratory symptoms. Following this clustering, processor 104 then generates diagnostic data based on the known diagnoses associated with this symptom cluster, such as Asthma or Pneumonia, and may suggest further diagnostic tests or evaluations to refine the diagnosis.

With continued reference to FIG. 1, processor 104 may generate diagnostic data 120 using a diagnostic machine-learning model. As used in the current disclosure, a "diagnostic machine-learning model" is a machine-learning model that is configured to generate diagnostic data 120, diagnostic machine-learning model may be consistent with the machine-learning model described below in FIG. 2. In an embodiment, a diagnostic machine learning model may include a classifier, as a described in greater detail herein below. A diagnostic machine learning model may be designed to analyze complex datasets and identify patterns or features that correlate with specific outcomes or categories. The diagnostic machine-learning model may be trained using historical data, which may allow them to predict or classify future or unseen data points into predefined categories based on their characteristics. For example, a diagnostic machine learning model might analyze a user dataset 108 to classify individuals as having a certain disease or not, based on inputs such as lab test results, symptoms, and demographic information. Inputs to the diagnostic machine-learning model may include user dataset 108, EHR 116, examples of diagnostic data 120, and the like. Outputs to the diagnostic machine-learning model may include diagnostic data 120 tailored to the user dataset 108. Diagnostic training data may include a plurality of data entries containing a plurality of inputs that are correlated to a plurality of outputs for training a processor by a machine-learning process. In an embodiment, diagnostic training data may include a plurality of user dataset 108 correlated to examples of diagnostic data 120, diagnostic training data may be received from database 300. Diagnostic training data may contain information about user dataset 108, EHR 116, examples of diagnostic data 120, and the like. In an embodiment, diagnostic training data may be iteratively updated as a function of the input and output results of past diagnostic machine-learning model or any other machine-learning model mentioned throughout this disclosure. The machine-learning model may be performed using, without limitation, linear machine-learning models such as without limitation logistic regression and/or naive Bayes machine-learning models, nearest neighbor machine-learning models such as k-nearest neighbors machine-learning models, support vector machines, least squares support vector machines, fisher's linear discriminant, quadratic machine-learning models, decision trees, boosted trees, random forest machine-learning model, and the like.

With continued reference to FIG. 1, predict one or more regions of interest (ROI) 124 within at least a pathology slide 112 as a function of the user dataset 108. As used in the current disclosure, a "region of interest" is a specific area within a pathology slide. The ROI 124 may be an area where it is desirable to conduct further analysis or examination. This ROI 124 may be identified within the broader context of a pathology slide, which may contain tissue samples subjected to microscopic examination to detect and study diseases, including cancer, infections, and other pathological conditions. The process of identifying ROIs 124 may consider the user dataset 108, which may include a variety of data inputs such as patient history, previous diagnoses, genetic information, and other relevant medical data. A ROI 124 may pinpoint areas on the pathology slide 112 that are most likely to yield valuable insights for the case at hand. This targeted approach may enable processor 104 to focus its efforts on the most promising sections of the slide, thereby enhancing the efficiency and accuracy of diagnostic and research workflows. In a non-limiting embodiment, examples of ROIs 124 may include large lesions, tumors, areas of necrosis, or significant inflammatory responses. These features may stand out due to their size and can often be visually distinguished from the surrounding healthy tissue. The ROI 124 may be selected because of its likelihood to contain important information relevant to the diagnosis, research, or study being conducted. This could be an area of the slide showing tumor cells, inflammatory responses, or unusual tissue architecture, and the like. Based on the analysis of diagnostic data 120, processor 104 may predict potential ROIs 124 on the pathology slide 112. This prediction may be grounded in the correlation between the identified features (e.g., specific symptoms or test results) and their manifestations in tissue morphology on the slide. For instance, if the diagnostic data 120 suggests a likelihood of cancer, the processor may target areas that typically exhibit tumor cells, abnormal tissue architecture, or other cancer-related characteristics.

With continued reference to FIG. 1, apparatus 100 employ an image processing module to identify a ROI 124 from the user dataset 108. As used in this disclosure, an "image processing module" is a component designed to process digital images. For example, and without limitation, an image processing module may be configured to compile plurality of images of a multi-layer scan to create an integrated image. In an embodiment, image processing module may include a plurality of software algorithms that can analyze, manipulate, or otherwise enhance an image, such as, without limitation, a plurality of image processing techniques as described below. In another embodiment, image processing module may slow include hardware components such as, without limitation, one or more graphics processing units (GPUs) that can accelerate the processing of large amount of images. In some cases, image processing module may be implemented with one or more image processing libraries such as, without limitation, OpenCV, PIL/Pillow, ImageMagick, and the like. Image processing module may include, be included in, or be communicatively connected to processor 104.

Still referring to FIG. 1, image processing module may be configured to receive a user dataset 108 that includes image data. In a non-limiting example, image processing module may be configured to receive images by generating a first image capture parameter, transmitting a command to optical system to take first image of a plurality of images with the first image capture parameter, generate a second image capture parameter, transmit a command to optical system to take second image of a plurality of images with the second image capture parameter, and receive, from optical system, first image and second image. In another non-limiting example, plurality of images may be taken by image capture devices using the same image capture parameter. Image capture parameter may be generated as a function of user input or processor 104.

Still referring to FIG. 1, a user dataset 108 that includes image data may be transmitted to the image processing module via any suitable electronic communication protocol, including without limitation packet-based protocols such as transfer control protocol-internet protocol (TCP-IP), file transfer protocol (FTP) or the like. Receiving images may include retrieval of images from a data store containing images as described below; for instance, and without limitation, images may be retrieved using a query that specifies a timestamp that images may be required to match.

Still referring to FIG. 1, image processing module may be configured to process images. In an embodiment, image processing module may be configured to compress and/or encode images to reduce the file size and storage requirements while maintaining the essential visual information needed for further processing steps as described below. In an embodiment, compression and/or encoding of plurality of images may facilitate faster transmission of images. In some cases, image processing module may be configured to perform a lossless compression on images, wherein the lossless compression may maintain the original image quality of images. In a non-limiting example, image processing module may utilize one or more lossless compression algorithms, such as, without limitation, Huffman coding, Lempel-Ziv-Welch (LZW), Run-Length Encoding (RLE), and/or the like to identify and remove redundancy in each image in a plurality of images without losing any information. In such embodiment, compressing and/or encoding each image of a plurality of images may include converting the file format of each image into PNG, GIF, lossless JPEG2000 or the like. In an embodiment, images compressed via lossless compression may be perfectly reconstructed to the original form (e.g., original image resolution, dimension, color representation, format, and the like) of images. In other cases, image processing module may be configured to perform a lossy compression on plurality of images, wherein the lossy compression may sacrifice some image quality of images to achieve higher compression ratios. In a non-limiting example, image processing module may utilize one or more lossy compression algorithms, such as, without limitation, Discrete Cosine Transform (DCT) in JPEG or Wavelet Transform in JPEG2000, discard some less significant information within images, resulting in a smaller file size but a slight loss of image quality of images. In such embodiment, compressing and/or encoding each image of a plurality of images may include converting the file format of each image into JPEG, WebP, lossy JPEG2000, or the like.

Still referring to FIG. 1, in an embodiment, processing images may include determining a degree of quality of depiction of a of an image or a plurality of images. In an embodiment, image processing module may determine a degree of blurriness of images. In a non-limiting example, image processing module may perform a blur detection by taking a Fourier transform, or an approximation such as a Fast Fourier Transform (FFT) of images and analyzing a distribution of low and high frequencies in the resulting frequency-domain depiction of images; for instance, and without limitation, numbers of high-frequency values below a threshold level may indicate blurriness. In another non-limiting example, detection of blurriness may be performed by convolving images, a channel of images, or the like with a Laplacian kernel; for instance, and without limitation, this may generate a numerical score reflecting a number of rapid changes in intensity shown in each image, such that a high score indicates clarity, and a low score indicates blurriness. In some cases, blurriness detection may be performed using a Gradient-based operator, which measures operators based on the gradient or first derivative of images, based on the hypothesis that rapid changes indicate sharp edges in the image, and thus are indicative of a lower degree of blurriness. In some cases, blur detection may be performed using Wavelet-based operator, which takes advantage of the capability of coefficients of the discrete wavelet transform to describe the frequency and spatial content of images. In some cases, blur detection may be performed using statistics-based operators take advantage of several image statistics as texture descriptors in order to compute a focus level. In other cases, blur detection may be performed by using discrete cosine transform (DCT) coefficients in order to compute a focus level of images from its frequency content. Additionally, or alternatively, image processing module may be configured to rank images according to degree of quality of depiction of a region of interest 124 and select a highest-ranking image from a plurality of images.

Still referring to FIG. 1, processing images may include enhancing at least a region of interest 124 via a plurality of image processing techniques to improve the quality (or degree of quality of depiction) of an image for better processing and analysis as described further in this disclosure. In an embodiment, image processing module may be configured to perform a noise reduction operation on an image, wherein the noise reduction operation may remove or minimize noise (arises from various sources, such as sensor limitations, poor lighting conditions, image compression, and/or the like), resulting in a cleaner and more visually coherent image. In some cases, noise reduction operation may be performed using one or more image filters; for instance, and without limitation, noise reduction operation may include Gaussian filtering, median filtering, bilateral filtering, and/or the like. Noise reduction operation may be done by image processing module, by averaging or filtering out pixel values in neighborhood of each pixel of an image to reduce random variations.

Still referring to FIG. 1, in another embodiment, image processing module may be configured to perform a contrast enhancement operation on an image. In some cases, an image may exhibit low contrast, which may, for example, make a feature difficult to distinguish from the background. Contrast enhancement operation may improve the contrast of an image by stretching the intensity range of the image and/or redistributing the intensity values (i.e., degree of brightness or darkness of a pixel in the image). In a non-limiting example, intensity value may represent the gray level or color of each pixel, scale from 0 to 255 in intensity range for an 8-bit image, and scale from 0 to 16,777,215 in a 24-bit color image. In some cases, contrast enhancement operation may include, without limitation, histogram equalization, adaptive histogram equalization (CLAHE), contrast stretching, and/or the like. Image processing module may be configured to adjust the brightness and darkness levels within an image to make a feature more distinguishable (i.e., increase degree of quality of depiction). Additionally, or alternatively, image processing module may be configured to perform a brightness normalization operation to correct variations in lighting conditions (i.e., uneven brightness levels). In some cases, an image may include a consistent brightness level across a region after brightness normalization operation performed by image processing module. In a non-limiting example, image processing module may perform a global or local mean normalization, where the average intensity value of an entire image or region of an image may be calculated and used to adjust the brightness levels.

Still referring to FIG. 1, in other embodiments, image processing module may be configured to perform a color space conversion operation to increase degree of quality of depiction. In a non-limiting example, in case of a color image (i.e., RGB image), image processing module may be configured to convert RGB image to grayscale or HSV color space. Such conversion may emphasize the differences in intensity values between a region of interest 124 and the background. Image processing module may further be configured to perform an image sharpening operation such as, without limitation, unsharp masking, Laplacian sharpening, high-pass filtering, and/or the like. Image processing module may use image sharpening operation to enhance the edges and fine details related to a region of interest 124 within an image by emphasizing high-frequency components within an image.

Still referring to FIG. 1, processing images may include isolating a region of interest 124 from the rest of an image as a function of plurality of image processing techniques. Images may include highest-ranking image selected by image processing module as described above. In an embodiment, plurality of image processing techniques may include one or more morphological operations, wherein the morphological operations are techniques developed based on set theory, lattice theory, topology, and random functions used for processing geometrical structures using a structuring element. A "structuring element," for the purpose of this disclosure, is a small matrix or kernel that defines a shape and size of a morphological operation. In some cases, structing element may be centered at each pixel of an image and used to determine an output pixel value for that location. In a non-limiting example, isolating a region of interest 124 from an image may include applying a dilation operation, wherein the dilation operation is a basic morphological operation configured to expand or grow the boundaries of objects (e.g., a cell, a lesion, and the like) in an image. In another non-limiting example, isolating a region of interest 124 from an image may include applying an erosion operation, wherein the erosion operation is a basic morphological operation configured to shrink or erode the boundaries of objects in an image. In another non-limiting example, isolating a region of interest 124 from an image may include applying an opening operation, wherein the opening operation is a basic morphological operation configured to remove small objects or thin structures from an image while preserving larger structures. In a further non-limiting example, isolating a region of interest 124 from an image may include applying a closing operation, wherein the closing operation is a basic morphological operation configured to fill in small gaps or holes in objects in an image while preserving the overall shape and size of the objects. These morphological operations may be performed by image processing module to enhance the edges of objects, remove noise, or fill gaps in a region of interest 124 before further processing.

With continued reference to FIG. 1, in an embodiment, isolating a region of interest 124 from an image may include utilizing an edge detection technique, which may detect one or more shapes defined by edges. An "edge detection technique," as used in this disclosure, includes a mathematical method that identifies points in a digital image, at which the image brightness changes sharply and/or has a discontinuity. In an embodiment, such points may be organized into straight and/or curved line segments, which may be referred to as "edges." Edge detection technique may be performed by image processing module, using any suitable edge detection algorithm, including without limitation Canny edge detection, Sobel operator edge detection, Prewitt operator edge detection, Laplacian operator edge detection, and/or Differential edge detection. Edge detection technique may include phase congruency-based edge detection, which finds all locations of an image where all sinusoids in the frequency domain, for instance as generated using a Fourier decomposition, may have matching phases which may indicate a location of an edge. Edge detection technique may be used to detect a shape of a region of interest 124 such as a cell, indicating a cell membrane or wall; in an embodiment, edge detection technique may be used to find closed figures formed by edges.

Still referring to FIG. 1, in a non-limiting example, isolating a region of interest 124 from an image may include determining a region of interest 124 via edge detection technique. A region of interest 124 may include a specific area within a digital image that contains information relevant to further processing as described below. In a non-limiting example, an image data located outside a region of interest 124 may include irrelevant or extraneous information. Such portion of an image containing irrelevant or extraneous information may be disregarded by image processing module, thereby allowing resources to be concentrated at a region of interest 124. In some cases, region of interest 124 may vary in size, shape, and/or location within an image. In a non-limiting example region of interest 124 may be presented as a circle around the nucleus of a cell. In some cases, region of interest 124 may specify one or more coordinates, distances, and the like, such as center and radius of a circle around the nucleus of a cell in an image. Image processing module may then be configured to isolate region of interest 124 from the image based on region of interest 124. In a non-limiting example, image processing module may crop an image according to a bounding box around a region of interest 124.

Still referring to FIG. 1, image processing module may be configured to perform a connected component analysis (CCA) on an image for region of interest 124 isolation. As used in this disclosure, a "connected component analysis (CCA)," also known as connected component labeling, is an image processing technique used to identify and label connected regions within a binary image (i.e., an image which each pixel having only two possible values: 0 or 1, black or white, or foreground and background). "Connected regions," as described herein, is a group of adjacent pixels that share the same value and are connected based on a predefined neighborhood system such as, without limitation, 4-connected or 8-connected neighborhoods. In some cases, image processing module may convert an image into a binary image via a thresholding process, wherein the thresholding process may involve setting a threshold value that separates the pixels of an image corresponding to region of interest 124 (foreground) from those corresponding to the background. Pixels with intensity values above the threshold may be set to 1 (white) and those below the threshold may be set to 0 (black). In an embodiment, CCA may be employed to detect and extract region of interest 124 by identifying a plurality of connected regions that exhibit specific properties or characteristics of the region of interest 124. Image processing module may then filter plurality of connected regions by analyzing plurality of connected regions properties such as, without limitation, area, aspect ratio, height, width, perimeter, and/or the like. In a non-limiting example, connected components that closely resemble the dimensions and aspect ratio of region of interest 124 may be retained, by image processing module as region of interest 124, while other components may be discarded. Image processing module may be further configured to extract region of interest 124 from an image for further processing as described below.

Still referring to FIG. 1, in an embodiment, isolating region of interest 124 from an image may include segmenting a region depicting a region of interest 124 into a plurality sub-regions. Segmenting a region into sub-regions may include segmenting a region as a function of region of interest 124 and/or CCA via an image segmentation process. As used in this disclosure, an "image segmentation process" is a process for partition a digital image into one or more segments, where each segment represents a distinct part of the image. Image segmentation process may change the representation of images. Image segmentation process may be performed by image processing module. In a non-limiting example, image processing module may perform a region-based segmentation, wherein the region-based segmentation involves growing regions from one or more seed points or pixels on an image based on a similarity criterion. Similarity criterion may include, without limitation, color, intensity, texture, and/or the like. In a non-limiting example, region-based segmentation may include region growing, region merging, watershed algorithms, and the like.

With continued reference to FIG. 1, processor 104 may identify an ROI 124 using an identification machine-learning model 128. As used in the current disclosure, a "identification machine-learning model" is a machine-learning model that is configured to generate ROI 124. Identification machine-learning model 128 may be consistent with the machine-learning model described below in FIG. 2. Inputs to the identification machine-learning model 128 may include user datasets 108, EHRs 116, diagnostic data 120, examples of ROIs 124, and the like. Outputs to the identification machine-learning model 128 may include ROIs 124 identified from the user dataset 108 and/or the diagnostic data 120. In an embodiment, identification machine-learning model 128 may be configured to identify ROIs 124 that are associated with the diagnosis/prognosis provided by diagnostic data 120. Identification machine-learning model 128 may narrow the type of ROIs 124 that it is looking for based on this information. Identification machine learning model 128 may identify subset of identification training data that reflects examples of ROIs 124 that have been associated with diagnosis/prognosis provided by diagnostic data 120. This filtering process may allow for the identification machine-learning model 128 to be more efficient.

With continued reference to FIG. 1, outputs to the identification machine-learning model 128 may define the ROI 124 in various manners. The ROI 124 may be defined using coordinates to outline the area precisely. For example, it could define the ROI 124 as a bounding box with coordinates (x_min, y_min)=(150, 200) for the top-left corner and (x_max, y_max)=(450, 500) for the bottom-right corner. This means the ROI 124 may span from point (150, 200) to (450, 500) on the pathology slide 112, capturing the specific tissue area of interest. Alternatively, if a segmentation mask approach is used, the system may generate a binary mask over the slide's image. In this mask, pixels within the (150, 200) to (450, 500) bounding box—representing the suspected cancerous tissue area—would be marked with a value of 1, indicating they're part of the ROI. In contrast, all other pixels outside this box would be marked with a value of 0, denoting they're not of immediate interest.

With continued reference to FIG. 1, identification training data may include a plurality of data entries containing a plurality of inputs that are correlated to a plurality of outputs for training a processor by a machine-learning process. In an embodiment, identification training data may include a plurality of pathology slides 112 and a plurality of user datasets 108 correlated to examples of ROIs 124. Identification training data may be received from database 300. Identification training data may contain information about user datasets 108, EHRs 116, diagnostic data 120, examples of ROI 124, and the like. In an embodiment, identification training data may be iteratively updated as a function of the input and output results of past identification machine-learning model 128 or any other machine-learning model mentioned throughout this disclosure. The machine-learning model may be performed using, without limitation, linear machine-learning models such as without limitation logistic regression and/or naive Bayes machine-learning models, nearest neighbor machine-learning models such as k-nearest neighbors machine-learning models, support vector machines, least squares support vector machines, fisher's linear discriminant, quadratic machine-learning models, decision trees, boosted trees, random forest machine-learning model, and the like.

With continued reference to FIG. 1, identification training data may include a collection of annotated pathology slide images. These images may be labeled to indicate areas that are of particular interest or relevance for diagnosing diseases. The quality, diversity, and accuracy of this training data may be valuable for developing a model that can reliably and accurately identify ROIs in new, unseen pathology slide images. The identification training data may include high-resolution images of pathology slides at various magnifications, capturing a wide range of tissue types and disease states. These images may be clear and free of artifacts to ensure the model can learn from accurate representations of the tissue. Identification training data may cover a broad spectrum of pathological conditions, including different types of cancers, inflammatory diseases, degenerative conditions, and infections, across various tissue types (e.g., breast, lung, liver, skin). Each image in the identification training data may be annotated to mark the ROIs, which could include tumor regions, areas of inflammation, necrosis, or other pathological features. Annotations might take the form of bounding boxes, segmentation masks, or point markers, depending on the model's design and the nature of the task (e.g., classification, detection, segmentation). Identification training data may include the accompanying clinical data to the slide, such as patient demographics, diagnosis, prognosis, and treatment outcomes, can enrich the training dataset, enabling the model to learn correlations between pathological features and clinical outcomes. To increase the diversity of the identification training data and improve the model's generalizability, images may be artificially augmented through techniques such as rotation, scaling, flipping, and color variation. This helps the model become invariant to such transformations, enhancing its performance on unseen images. In some embodiment, separate sets of annotated images may be reserved for validating and testing the model. These datasets are crucial for tuning model parameters and evaluating the model's performance in identifying ROIs on pathology slides.

With continued reference to FIG. 1, identification training data may include a set of associations textual data and the image data within the user dataset 108. As used in the current disclosure, "association" refers to the relationship or connection established between two or more data types. This may include a relationship or connection established between image data and textual data. It involves linking or integrating the image data with descriptive or explanatory textual data of the user dataset 108 to provide additional context, enhance understanding, and convey relevant information. In an embodiment, a set of associations may include an identification of a ROI 124 within the image data and its accompanying textual data that provides context for ROI. In a non-limiting example, identification training data may include an identification of a group of ROIs 124 within a plurality of image data.

With continued reference to FIG. 1, image processing techniques may be used to improve upon machine learning model training processes. By filtering and enhancing the images within the user dataset 108, the overall quality of the dataset improves. This improvement may directly impact the performance of machine learning algorithms, as clearer, more defined images allow for more accurate feature extraction and classification. For example, morphological operations can help isolate and emphasize relevant features within the training data, reducing noise and irrelevant information. Consequently, models trained on this high-quality data are better equipped to generalize from the training dataset to real-world applications, leading to increased accuracy and reliability in tasks like object recognition, segmentation, and classification.

Incorporating the user feedback may include updating the training data by removing or adding correlations of user data to a path or resources as indicated by the feedback. Any machine-learning model as described herein may have the training data updated based on such feedback or data gathered using a web crawler as described above. For example, correlations in training data may be based on outdated information wherein, a web crawler may update such correlations based on more recent resources and information.

With continued reference to FIG. 1, processor 104 may use user feedback to train the machine-learning models and/or classifiers described above. For example, machine-learning models and/or classifiers may be trained using past inputs and outputs of identification machine-learning model 128. In some embodiments, if user feedback indicates that an output of machine-learning models and/or classifiers was "bad," then that output and the corresponding input may be removed from training data used to train machine-learning models and/or classifiers, and/or may be replaced with a value entered by, e.g., another value that represents an ideal output given the input the machine learning model originally received, permitting use in retraining, and adding to training data; in either case, classifier may be retrained with modified training data as described in further detail below. In some embodiments, training data of classifier may include user feedback.

With continued reference to FIG. 1, in some embodiments, an accuracy score may be calculated for the machine-learning model and/or classifier using user feedback. For the purposes of this disclosure, "accuracy score," is a numerical value concerning the accuracy of a machine-learning model. For example, the accuracy/quality of the output of the identification machine-learning model 128 may be averaged to determine an accuracy score. In some embodiments, an accuracy score may be determined for identification of ROIs 124 within pathology slide 112. Accuracy score or another score as described above may indicate a degree of retraining needed for a machine-learning model and/or classifier. Processor 104 may perform a larger number of retraining cycles for a higher number (or lower number, depending on a numerical interpretation used), and/or may collect more training data for such retraining. The discussion within this paragraph and the paragraphs preceding this paragraph may apply to both the identification machine-learning model 128 and/or any other machine-learning model/classifier mentioned herein.

With continued reference to FIG. 1, in an embodiment, identification machine-learning model 128 may comprise a deep neural network (DNN). As used in this disclosure, a "deep neural network" is defined as a neural network with two or more hidden layers. Neural network is described in further detail below with reference to FIGS. 4-5. In a non-limiting example, identification machine-learning model 128 may include a convolutional neural network (CNN.) Identifying one or more ROIs 124 using an identification machine-learning model 128 may include training CNN using unique identifier training data and identifying one or more ROIs 124 from the user dataset 108 using trained CNN. A "convolutional neural network," for the purpose of this disclosure, is a neural network in which at least one hidden layer is a convolutional layer that convolves inputs to that layer with a subset of inputs known as a "kernel," along with one or more additional layers such as pooling layers, fully connected layers, and the like. In some cases, CNN may include, without limitation, a deep neural network (DNN) extension. Mathematical (or convolution) operations performed in the convolutional layer may include convolution of two or more functions, where the kernel may be applied to input data e.g., user dataset 108 through a sliding window approach. In some cases, convolution operations may enable processor 104 to detect local/global patterns, edges, textures, and any other features described herein within user dataset 108. Spatial features may be passed through one or more activation functions, such as without limitation, Rectified Linear Unit (ReLU), to introduce non-linearities into the processing step of identifying one or more ROIs 124. Additionally, or alternatively, CNN may also include one or more pooling layers, wherein each pooling layer is configured to reduce the dimensionality of input data while preserving essential features within the input data. In a non-limiting example, CNN may include one or more pooling layer configured to reduce the dimensions of feature maps by applying downsampling, such as max-pooling or average pooling, to small, non-overlapping regions of one or more features.

Still referring to FIG. 1, CNN may further include one or more fully connected layers configured to combine features extracted by the convolutional and pooling layers as described above. In some cases, one or more fully connected layers may allow for higher-level pattern recognition. In a non-limiting example, one or more fully connected layers may connect every neuron (i.e., node) in its input to every neuron in its output, functioning as a traditional feedforward neural network layer. In some cases, one or more fully connected layers may be used at the end of CNN to perform high-level reasoning and produce the final output such as, without limitation, one or more ROIs 124. Further, each fully connected layer may be followed by one or more dropout layers configured to prevent overfitting, and one or more normalization layers to stabilize the learning process described herein.

With continued reference to FIG. 1, in an embodiment, training the identification machine-learning model 128 (i.e., CNN) may include selecting a suitable loss function to guide the training process. In a non-limiting example, a loss function that measures the difference between the identified one or more ROIs 124 and the ground truth 3D structure e.g., Unique identifier training data may be used, such as, without limitation, mean squared error (MSE) or a custom loss function may be designed for one or more embodiments described herein. Additionally, or alternatively, optimization algorithms, such as stochastic gradient descent (SGD), may then be used to adjust the identification machine-learning model's 128 parameters to minimize such loss. In a further non-limiting embodiment, instead of directly identifying one or more ROIs 124, identification machine-learning model 128 may be trained as a regression model to identify information associated with the one or more ROIs 124. Additionally, CNN may be extended with additional deep learning techniques, such as recurrent neural networks (RNNs) or attention mechanism, to capture additional features and/or data relationships within input data. These extensions may further enhance the accuracy and robustness of the identification of the one or more ROIs 124.

With continued reference to FIG. 1, identify at least one scan parameter 132 as a function of the one or more regions of interest 124. As used in the current disclosure, a "scan parameter" refers to the specific settings or conditions under which a camera captures images of microscope slides. A scan parameter 132 may be described as a set of instructions or settings tailored to optimally capture the details of the specified ROI 124 during the scanning process. These parameters may ensure that the digital image produced is of the highest quality and resolution necessary for accurate analysis and diagnosis. Examples of scan parameters may include resolution, focus, magnification, illumination, the field of view, and the like. Adjusting these parameters may be valuable for optimizing image quality, especially when scanning slides for pathological analysis, as it allows for clearer visualization of critical features necessary for accurate diagnosis. A scan parameter 132 may specify the level of detail captured in the scan. For ROIs 124 requiring detailed examination (e.g., cellular structures, tumor margins), a higher resolution may be selected to ensure that fine details are visible and distinguishable in the scanned image. In an embodiment, a scan parameter 132 may include information about the color balance and contrast of the camera. This may be adjusted to enhance the visibility of specific stains or tissue characteristics within the ROI. This parameter ensures that the digital scan accurately represents the slide's coloration, aiding in the identification and analysis of pathological features. Color balance adjustments ensure that the colors in the scanned image accurately reflect the colors of the stained tissue, which is critical for correct interpretation. The optimal settings for color balance depend on the staining methods used and the lighting conditions. Adjusting contrast settings may help in highlighting subtle differences in tissue density and structure, making it easier to distinguish between different cellular components and tissue types. Optimal contrast settings may vary based on the tissue characteristics and the specific details that need to be visualized. In an embodiment, a scan parameter 132 may include information about the scan area. The scan area may define the physical boundaries of the scan, ensuring that the entire ROI 124 is captured within the digital image. This might involve automatically adjusting the scan area based on the ROI's 124 size and location on the slide. Determining scan parameters 132 from a ROI 124 through computational means may involve a series of steps that leverage image analysis, machine learning algorithms, and pattern recognition techniques. The goal is to optimize the scanning process to capture the highest quality image of the ROI, ensuring that all relevant pathological details are clearly visible and accurately represented in the digital image.

With continued reference to FIG. 1, in situations where the Region of Interest (ROI) 124 cannot be accurately identified, the system may incorporate a fail-safe mechanism. If the system fails to identify the ROI 124 automatically, it may prompt a manual intervention or defaults to a pre-set scan parameter 132. This fail-safe approach ensures continuity in the scanning process, preventing delays and maintaining efficiency. The default scan parameter 132 may be a generalized setting designed to capture a broad range of features across various types of specimens. This setting may aim to produce a sufficiently detailed image that can either be manually analyzed later or re-assessed by the system for ROI 124 identification. The default scan parameter may include a moderate resolution and contrast level, along with a standardized field of view and illumination setting, to ensure that, despite the lack of specific ROI 124 targeting, the resulting scan is of high enough quality for subsequent review or analysis.

With continued reference to FIG. 1, a scan parameter 132 may include modifying the resolution camera. As used in the current disclosure, "resolution" pertains to the ability of an imaging system to distinguish between fine details within the sample being observed. The resolution may influence the quality of the images produced, impacting the level of detail visible for analysis and diagnosis. High-resolution imaging may be valuable for identifying and analyzing microscopic structures such as individual cells, cellular organelles, and tissue architecture. This level of detail may be needed for accurate diagnosis and understanding of various diseases, including cancer and infectious diseases. Slides may be scanned to create digital images that can be viewed, shared, and analyzed electronically. The resolution of these digital images directly affects the ability of pathologists to examine and interpret the slides remotely, making high resolution vital for reliable diagnosis. High-resolution images are also crucial for automated image analysis algorithms, including machine learning models used to identify patterns, classify tissues, and detect abnormalities. These models require detailed images to accurately learn and predict pathological features. When adjusting the resolution of the camera the processor may adjust the spatial resolution. Spatial resolution refers to the smallest distinguishable detail that can be seen in an image. In digital pathology images, it's often measured in micrometers per pixel (μm/pixel), indicating the size of the smallest feature that one pixel represents. High spatial resolution means smaller features can be resolved, leading to clearer and more detailed images. The optimal resolution for scanning may be determined based on the smallest detail that needs to be resolved in the image. Processor 104 may determine the smallest detail that needs to be seen in an image based on matching the diagnostic data 120 to one or more features that may be present within the pathology slide 112. Processor 104 analyzes diagnostic data 120, correlating it with known pathological features that may be present within the pathology slide 112. By matching these diagnostic criteria to specific features—such as cellular structures, tissue patterns, or pathological abnormalities—the processor calculates the minimum resolution needed to clearly resolve these details. This tailored approach ensures that the scanned image is of sufficient quality for accurate diagnosis, optimizing the balance between image clarity and efficient data management.

With continued reference to FIG. 1, a scan parameter 132 may include focus depth. As used in the current disclosure, "focus depth" refers to the range within which all elements in the field of view are in sharp focus. This concept may be relevant when dealing with three-dimensional or thick specimens, where different layers or structures of the tissue may be located at varying distances from the lens. Properly adjusting the focus depth ensures that the details across these layers are captured clearly in the image. In microscopy, managing focus depth effectively may be valuable for accurate diagnosis and analysis. In a non-limiting example, in tissue samples with varying thickness or topography, the focus depth ensures that the ROI 124 is captured in sharp focus across its entirety. This might involve setting a specific focus plane or utilizing z-stacking techniques to compose multiple images at different focal depths. Z-stacking may involve taking multiple images at different focal planes throughout the specimen. These images may then be digitally combined into a single composite image where elements at various depths are all in focus. This method is particularly useful for examining samples with significant three-dimensional structures. In some cases, focus depth may be modified using auto-focus systems. Auto-focus systems may automatically adjust the lens to optimize focus depth for a given field of view. These systems can rapidly assess the focal plane and adjust the lens position to capture the clearest possible image of the ROI. Determining the optimal focus depth ensures that all parts of the ROI are in sharp focus. Techniques like z-stacking, where multiple images at different focal depths are combined, may be employed to achieve a uniformly focused image across the entire depth of the sample.

With continued reference to FIG. 1, a scan parameter 132 may include magnification level. As used in the current disclosure, a "magnification level" refers to the degree to which an image is enlarged or amplified in size compared to its original. The magnification level is typically expressed as a multiplier (e.g., 10×, 40×, 100×), indicating how many times larger the observed image appears compared to its actual size. For example, a 10× magnification level means that the image is magnified to appear ten times larger than its real size, allowing the observer to see details that are not visible to the naked eye. A scan parameter 132 can be characterized and prioritized based on the magnification level. The magnification level may influence the detail and type of information that can be observed and analyzed within a pathology slide 112. Understanding ROIs 124 at different magnification levels may be valuable for thorough pathological assessment. Magnification level may be described as a low magnification, medium magnification, high magnification, ultrahigh magnification, and the like. This can range from low magnification, which provides an overview of tissue architecture and organization, to high magnification, which allows for detailed cellular and subcellular analyses. The magnification level of the pathology slide may dictate the scale and type of ROIs that are emphasized during microscopic examination. Lower magnifications may be used for broad assessments of tissue architecture and the identification of large pathological features, while higher magnifications may focus on detailed cellular and subcellular features. The choice of magnification may be guided by the diagnostic data 120. Selection of the magnification level may be related to the selection of the resolution. Selection of the magnification level may be determined based on the level of detail required. The determination of the magnification level for scanning may be guided by the requirement to visualize specific diagnostic features identified within the pathology slide 112, as informed by diagnostic data 120. Processor 104 assesses the diagnostic data, which encompasses patient history, pathological findings, and any known microscopic features associated with the condition under investigation. By aligning this data with the scale of features present on the slide-ranging from broad tissue architecture to minute cellular details—the processor may select a magnification level that optimizes visibility of these critical features. This calculated selection ensures that the magnification is neither too low, potentially missing fine details, nor excessively high, which could limit the field of view unnecessarily. The goal is to achieve a precise balance that facilitates comprehensive diagnostic analysis while maximizing the efficiency of the scanning process.

With continued reference to FIG. 1, low magnification may be between 1× and 10× magnification. At low magnification, ROIs 124 may be defined by the overall layout of the tissue, including the distribution of various tissue types, the presence of large pathological features such as tumors, cysts, or areas of necrosis, and the general pattern of tissue organization. At low magnification, Large-scale abnormalities such as tumors, cysts, or significant inflammatory infiltrates may be easily identified.

With continued reference to FIG. 1, medium magnification may be between 10× and 40× magnification. Medium magnification may allow for closer examination of tissue organization, including the arrangement of glands, blood vessels, and connective tissue. ROIs 124 at this level may pinpoint areas with abnormal tissue patterns or structures indicative of pathological processes. While not providing the highest resolution, medium magnification may begin to reveal cellular details such as the shape and size of cells, basic cell types, and some intracellular components, aiding in the identification of areas warranting closer inspection.

With continued reference to FIG. 1, high magnification may be between 40× and 100× magnification. High magnification may be essential for examining the fine details of cells within ROIs 124, including the morphology of nuclei, cytoplasmic details, and the presence of specific cellular inclusions or extracellular matrix alterations. At this level, specific pathological features such as mitotic figures, signs of cellular dysplasia, viral inclusion bodies, and fine vascular changes can be observed. High magnification may be used for diagnosing many conditions, including cancer, by allowing the identification of malignant cell characteristics.

With continued reference to FIG. 1, ultra-high magnification may be in excess of 100× magnification. Ultra-high magnification, may often be achieved with oil immersion lenses, allows for the visualization of intracellular organelles, detailed nuclear features such as nucleoli, chromatin pattern, and subtle cytoplasmic details. This level is particularly useful for identifying small microorganisms (e.g., bacteria, fungi, parasites) and for assessing fine cellular alterations that are critical for specific diagnoses.

With continued reference to FIG. 1, processor 104 may include scan parameter 132 using a parameter machine-learning model 136. As used in the current disclosure, a "parameter machine-learning model" is a machine-learning model that is configured to generate scan parameter 132, parameter machine-learning model 136 may be consistent with the machine-learning model described below in FIG. 2. Inputs to the parameter machine-learning model 136 may include user datasets 108, EHRs 116, diagnostic data 120, ROIs 124, examples of scan parameter 132, and the like. Outputs to the parameter machine-learning model 136 may include scan parameter 132 tailored to the ROI 124, parameter training data may include a plurality of data entries containing a plurality of inputs that are correlated to a plurality of outputs for training a processor by a machine-learning process. In an embodiment, parameter training data may include a plurality of ROI 124 correlated to examples of scan parameter 132, parameter training data may be received from database 300, parameter training data may contain information about user datasets 108, EHRs 116, diagnostic data 120, ROIs 124, examples of scan parameter 132, and the like. In an embodiment, parameter training data may be iteratively updated as a function of the input and output results of past parameter machine-learning model 136 or any other machine-learning model mentioned throughout this disclosure. The machine-learning model may be performed using, without limitation, linear machine-learning models such as without limitation logistic regression and/or naive Bayes machine-learning models, nearest neighbor machine-learning models such as k-nearest neighbors machine-learning models, support vector machines, least squares support vector machines, fisher's linear discriminant, quadratic machine-learning models, decision trees, boosted trees, random forest machine-learning model, and the like.

Referring still to FIG. 1, apparatus 100 may be equipped to scan pathology slides 112 using an image capture device 140. As used in the current disclosure, an "image capture device" is a tool engineered to detect electromagnetic radiation, including but not limited to visible light, and to create a visual representation of this radiation. Such a device may incorporate various optical components. Examples of these optics, which are not limited to, encompass spherical lenses, aspherical lenses, reflectors, polarizers, filters, windows, aperture stops, among others. Additionally, an image capture device 140 might feature an image sensor, with examples including, but not restricted to, digital image sensors like charge-coupled device (CCD) sensors and complementary metal-oxide-semiconductor (CMOS) sensors, as well as chemical and analog image sensors, including film. It's also possible for an image capture device 140 to be responsive to electromagnetic radiation beyond the visible spectrum, such as infrared radiation. In a non-limiting example, an image capture device 140 may include an automated microscope.

Still referring to FIG. 1, in some embodiments, apparatus 100 may include a machine vision system that includes at least an image capture device 140. A machine vision system may use images from at least an image capture device 140, to make a determination about a scene, space, and/or object. For example, in some cases a machine vision system may be used for world modeling or registration of objects within a space. In some cases, registration may include image processing, such as without limitation object recognition, feature detection, edge/corner detection, and the like. Non-limiting example of feature detection may include scale invariant feature transform (SIFT), Canny edge detection, Shi Tomasi corner detection, and the like. In some cases, registration may include one or more transformations to orient an image capture device 140 frame (or an image or video stream) relative a three-dimensional coordinate system; exemplary transformations include without limitation homography transforms and affine transforms. In an embodiment, registration of first frame to a coordinate system may be verified and/or corrected using object identification and/or computer vision, as described above. For instance, and without limitation, an initial registration to two dimensions, represented for instance as registration to the x and y coordinates, may be performed using a two-dimensional projection of points in three dimensions onto a first frame, however. A third dimension of registration, representing depth and/or a z axis, may be detected by comparison of two frames; for instance, where first frame includes a pair of frames captured using a pair of image capture device 140s (e.g., stereoscopic image capture device also referred to in this disclosure as stereo-image capture device), image recognition and/or edge detection software may be used to detect a pair of stereoscopic views of images of an object; two stereoscopic views may be compared to derive z-axis values of points on object permitting, for instance, derivation of further z-axis points within and/or around the object using interpolation. This may be repeated with multiple objects in field of view, including without limitation environmental features of interest identified by object classifier and/or indicated by an operator. In an embodiment, x and y axes may be chosen to span a plane common to two image capture device 140s used for stereoscopic image capturing and/or an xy plane of a first frame; a result, x and y translational components and ø may be pre-populated in translational and rotational matrices, for affine transformation of coordinates of object, also as described above. Initial x and y coordinates and/or guesses at transformational matrices may alternatively or additionally be performed between first frame and second frame, as described above. For each point of a plurality of points on object and/or edge and/or edges of object as described above, x and y coordinates of a first stereoscopic frame may be populated, with an initial estimate of z coordinates based, for instance, on assumptions about object, such as an assumption that ground is substantially parallel to an xy plane as selected above. Z coordinates, and/or x, y, and z coordinates, registered using image capturing and/or object identification processes as described above may then be compared to coordinates predicted using initial guess at transformation matrices; an error function may be computed using by comparing the two sets of points, and new x, y, and/or z coordinates, may be iteratively estimated and compared until the error function drops below a threshold level. In some cases, a machine vision system may use a classifier, such as any classifier described throughout this disclosure.

With continued reference to FIG. 1, processor 104 generates a digitized slide 144 by scanning the at least a pathology slide 112 as a function the at least one scan parameter 132. As used in the current disclosure, a "digitized slide" is a digital representation of the at least a pathology slide 112. The digitized slide 144 may be composed of a collection of images derived from the original pathology slide 112. These images may be carefully curated to showcase the most significant features of the pathology slide 112. Such features may be valuable for diagnostic purposes, research, and educational uses. These features may include the ROI 124. The ROI 124 could be an area on the pathology slide that contains key information about the disease or condition being studied. It might include specific cell types, structures, or abnormalities that are critical for understanding the pathology. The digitized slide 144 enables easier access and manipulation of the slide's data. For example, it can be zoomed in for closer inspection of the ROI 124, shared with other professionals for consultation, stored in digital archives for future reference, used as training data for a machine learning model, and the like. In an embodiment, at least a pathology slide may be scanned in the same or a substantially similar manner as slide referenced in U.S. Non-provisional patent application Ser. No. 18/226,058, filed on Jul. 25, 2023, and titled "IMAGING DEVICE AND METHOD FOR IMAGE GENERATION OF A SPECIMEN," which is incorporated by reference herein in its entirety.

With continued reference to FIG. 1, processor 104 may prepare the image capture device 140 to scan the at least a pathology slide 112 as a function the at least one scan parameter 132. This preparation may involve adjusting the device's parameters according to predefined scan parameters 132. Processor 104 may adjust a wide range of settings, including resolution, color depth, focus, brightness, contrast levels, and the like of the image capture device 140. This may be done with the goal of tailoring the scanning process to the specific requirements of the pathology slide 112 being scanned. This may include adjusting the settings of an image capture device 140 to capture ROIs 124 within the pathology slide 124. These adjustments may assist in capturing the intricate details of the slide, especially when considering the diverse nature of pathological specimens, which can vary significantly in terms of color, thickness, and detail. Once the scan parameters 132 are set, the image capture device 140 may proceed to scan the pathology slide 112. This scanning can be comprehensive, covering the entire slide to ensure no detail is missed, or it can be targeted, focusing specifically on identified ROIs 124. These ROIs are areas on the slide deemed most relevant for diagnosis or study, possibly containing specific cell types or structures indicative of disease or health. As images of the slide are captured, they may undergo a process of quality control overseen by the processor 104. This may involve checking the images for clarity, focus, and overall quality to ensure they meet the required standards for diagnostic purposes. If the initial images do not meet these standards, adjustments to the scan parameters can be made in real-time. This capability for real-time adjustments is critical for adapting to any unforeseen challenges that arise during the scanning process, such as variations in slide thickness or staining quality, ensuring that the final digitized slide is of the highest possible quality. The captured images are processed and stored, forming the digitized slide. This digital format offers several advantages over traditional microscopy, including the ability to easily share slides for consultation, enhanced capabilities for zooming and analyzing specific features, and efficient storage and retrieval.

With continued reference to FIG. 1, processor 104 may be configured to scan the pathology slide 112 in a single pass. Scanning a pathology slide 112 in a single pass may be a streamlined and efficient process, designed to capture a high-quality digital representation of the slide in one continuous operation. This method contrasts with multi-pass scanning techniques that might scan a slide in sections or require multiple scans to capture different focal planes or regions of interest 124. Once the system is image capture device 140 according to the slide parameters 132, the scanning process may commence. The single-pass approach aims to capture the entire slide, including all relevant features and ROIs, in one uninterrupted scan. This may be ideal do to its increased efficiency and the reduction the time and resources needed for scanning while minimizing the risk of artifacts or inconsistencies that could arise from multiple scans. As the slide is scanned, the image capture device 140 may collect a continuous stream of data, capturing a comprehensive digital image of the slide. Advanced optics and high-resolution sensors may enable the image capture device 140 to record fine details such as cellular structures, tissue organization, and pathological abnormalities. The collected data may be processed, stitching together the continuous image data into a cohesive, high-resolution digital slide. In an embodiment, at least a pathology slide may be scanned in the same or a substantially similar manner as the slide referenced in U.S. Non-provisional patent application Ser. No. 18/382,769, filed on Oct. 23, 2023, and titled "SYSTEM AND METHOD OF DIGITIZING A SLIDE," which is incorporated by reference herein in its entirety.

With continued reference to FIG. 1, processor 104 a digitized slide 144 may include a plurality of slide data 148. As used in the current disclosure, "slide data" is a set of textual data that describes or provides context to what is depicted within the slide. Slide data 148 may include descriptive text that highlights specific features or areas of interest within the slide, such as particular cell types, tissue abnormalities, or regions of interest (ROIs) that are crucial for diagnosis or research. Slide data 148 may be attached to the digitized slide 144 in the form of metadata. This may include information about the slide's origin, preparation, staining, and scanning process. This can include the slide's source (patient information, if applicable and anonymized), the staining technique used, the date of slide preparation and digitization, and the parameters of the scanning process (resolution, magnification, etc.). In some cases, diagnostic information may also be included within the slide data 148. This may include preliminary findings, diagnosis, or comments from the pathologist or researcher who reviewed the slide. This might also include predictions or classifications from automated image analysis algorithms. In generating slide data 148 for a digitized slide 144, processor 104 may analyze, interpret, and contextualize the visual content of digitized slide 144. Processor 104 may employ information that is represented in the user dataset 108. To generate slide data 148, processor 104 may apply image analysis techniques, as discussed in greater detail herein above, to identify and catalog key features that are depicted within the digitized slide 144, such as specific cell types, tissue abnormalities, or notable structures. This identification can be based on pattern recognition, machine learning algorithms, or predefined criteria set by pathologists or researchers. For annotating specific features or regions of interest (ROIs) within the slide, the processor 104 may use coordinates or markers to link textual descriptions directly to the corresponding locations on the digitized slide 144. These annotations can describe the morphology of cells, the distribution of tissues, or highlight areas warranting further examination. The software ensures these annotations are scalable and visible across different magnification levels, maintaining their relevance as users zoom in or out of the image.

With continued reference to FIG. 1, processor 104 may attach the slide data 148 to the digitized slide 144. Attaching slide data 148 to the digitized slide 144 may involve embedding this information within the file structure of the digital slide 144 or linking it to a database entry corresponding to the slide. This embedded or linked slide data 148 may then be accessible through digital pathology software, allowing users to view the slide alongside its descriptive text and annotations. This may allow for the display of slide data 148 in a panel or overlay that can be toggled on or off, ensuring that the textual data enhances, rather than obstructs, the visual examination of the slide. As additional analyses are performed or new information becomes available, the processor 104 can append this to the existing slide data 148, ensuring that the digitized slide remains a living document enriched with the most current insights and findings.

Still referring to FIG. 1, processor 104 may be configured to display the digitized slide 144 using a display device 152. As used in the current disclosure, a "display device" is a device that is used to display content. A display device 152 may include a user interface. A "user interface," as used herein, is a means by which a user and a computer system interact; for example, through the use of input devices and software. A user interface may include a graphical user interface (GUI), command line interface (CLI), menu-driven user interface, touch user interface, voice user interface (VUI), form-based user interface, any combination thereof, and the like. A user interface may include a smartphone, smart tablet, desktop, or laptop operated by the user. In an embodiment, the user interface may include a graphical user interface. A "graphical user interface (GUI)," as used herein, is a graphical form of user interface that allows users to interact with electronic devices. In some embodiments, GUI may include icons, menus, other visual indicators, or representations (graphics), audio indicators such as primary notation, and display information and related user controls. A menu may contain a list of choices and may allow users to select one from them. A menu bar may be displayed horizontally across the screen such as pull-down menu. When any option is clicked in this menu, then the pull-down menu may appear. A menu may include a context menu that appears only when the user performs a specific action. An example of this is pressing the right mouse button. When this is done, a menu may appear under the cursor. Files, programs, web pages and the like may be represented using a small picture in a graphical user interface. For example, links to decentralized platforms as described in this disclosure may be incorporated using icons. Using an icon may be a fast way to open documents, run programs etc. because clicking on them yields instant access. Information contained in user interface may be directly influenced using graphical control elements such as widgets. A "widget," as used herein, is a user control element that allows a user to control and change the appearance of elements in the user interface. In this context a widget may refer to a generic GUI element such as a check box, button, or scroll bar to an instance of that element, or to a customized collection of such elements used for a specific function or application (such as a dialog box for users to customize their computer screen appearances). User interface controls may include software components that a user interacts with through direct manipulation to read or edit information displayed through user interface. Widgets may be used to display lists of related items, navigate the system using links, tabs, and manipulate data using check boxes, radio boxes, and the like.

Figure 2:
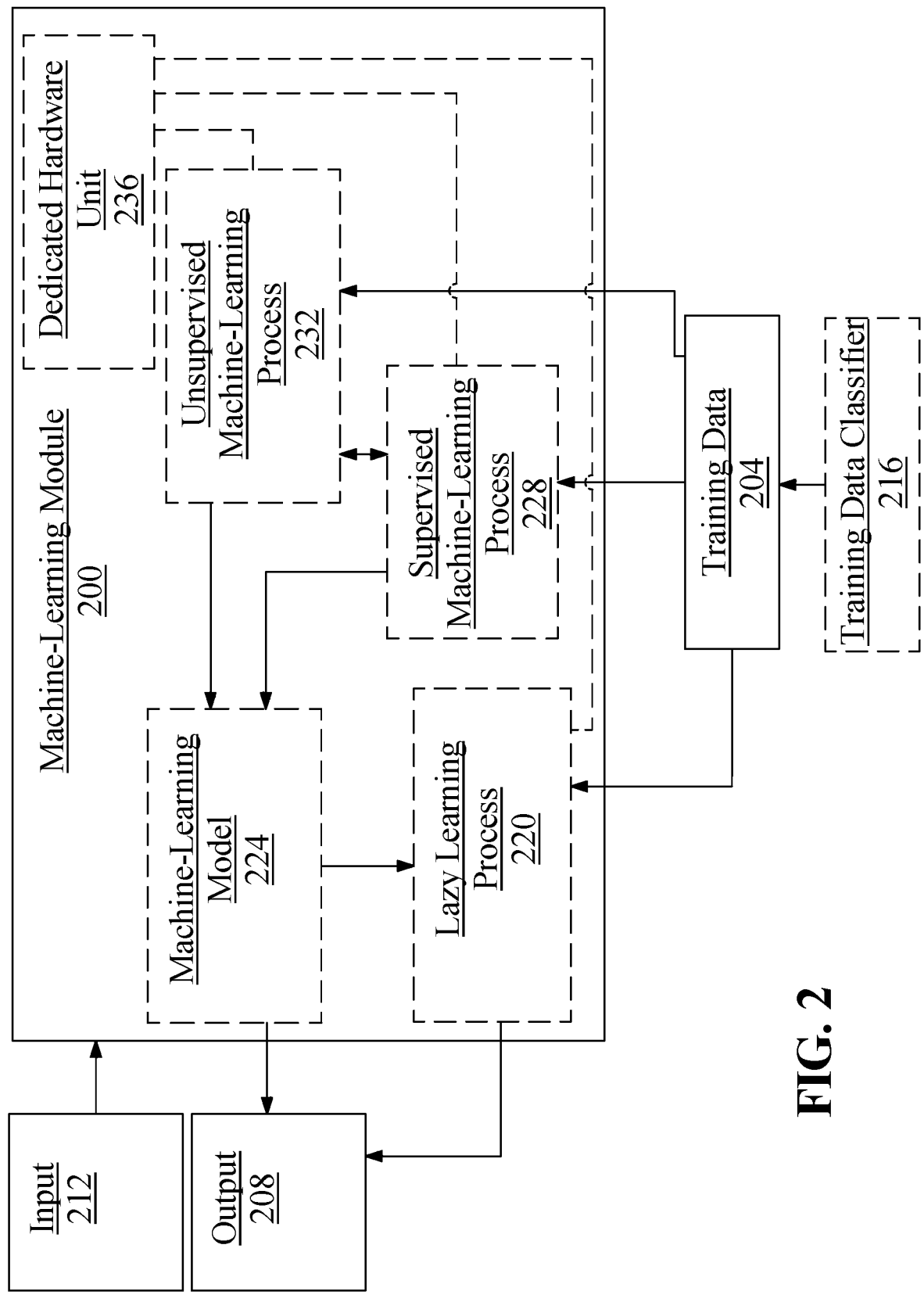
FIG. 2 is a block diagram of an exemplary machine-learning process.

Referring now to FIG. 2, an exemplary embodiment of a machine-learning module 200 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 204 to generate an algorithm instantiated in hardware or software logic, data structures, and/or functions that will be performed by a computing device/module to produce outputs 208 given data provided as inputs 212; this is in contrast to a non-machine learning software program where the commands to be executed are determined in advance by a user and written in a programming language.

Still referring to FIG. 2, "training data," as used herein, is data containing correlations that a machine-learning process may use to model relationships between two or more categories of data elements. For instance, and without limitation, training data 204 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 204 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 204 according to various correlations; correlations may indicate causative and/or predictive links between categories of data elements, which may be modeled as relationships such as mathematical relationships by machine-learning processes as described in further detail below. Training data 204 may be formatted and/or organized by categories of data elements, for instance by associating data elements with one or more descriptors corresponding to categories of data elements. As a non-limiting example, training data 204 may include data entered in standardized forms by persons or processes, such that entry of a given data element in a given field in a form may be mapped to one or more descriptors of categories. Elements in training data 204 may be linked to descriptors of categories by tags, tokens, or other data elements; for instance, and without limitation, training data 204 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 2, training data 204 may include one or more elements that are not categorized; that is, training data 204 may not be formatted or contain descriptors for some elements of data. Machine-learning algorithms and/or other processes may sort training data 204 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 204 to be made applicable for two or more distinct machine-learning algorithms as described in further detail below. Training data 204 used by machine-learning module 200 may correlate any input data as described in this disclosure to any output data as described in this disclosure. As a non-limiting illustrative example, a plurality of user datasets as inputs correlated to examples of regions of interest as outputs.

Further referring to FIG. 2, training data may be filtered, sorted, and/or selected using one or more supervised and/or unsupervised machine-learning processes and/or models as described in further detail below; such models may include without limitation a training data classifier 216. Training data classifier 216 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 200 may generate a classifier using a classification algorithm, defined as a processes whereby a computing device and/or any module and/or component operating thereon derives a classifier from training data 204. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 216 may classify elements of training data according to the users medical history or diagnostic data.

With further reference to FIG. 2, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Still referring to FIG. 2, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may be identified as having poor quality data, where "poor quality" is defined as having a signal to noise ratio below a threshold value.

As a non-limiting example, and with further reference to FIG. 2, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity, and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 2, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively, or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 2, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean upside-effects of compression.

Still referring to FIG. 2, machine-learning module 200 may be configured to perform a lazy-learning process 220 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 204. Heuristic may include selecting some number of highest-ranking associations and/or training data 204 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively, or additionally, and with continued reference to FIG. 2, machine-learning processes as described in this disclosure may be used to generate machine-learning models 224. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 224 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 224 may be generated by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 2, machine-learning algorithms may include at least a supervised machine-learning process 228. At least a supervised machine-learning process 228, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include user dataset 108 as described above as inputs one or more regions of interest as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 204. Persons skilled in the art, upon reviewing the entirety of this disclosure, will be aware of various possible variations of at least a supervised machine-learning process 228 that may be used to determine relation between inputs and outputs. Supervised machine-learning processes may include classification algorithms as defined above.

With further reference to FIG. 2, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively, or additionally, one or more errors and/or error function values evaluated in training iterations may be compared to a threshold.

Still referring to FIG. 2, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 2, machine learning processes may include at least an unsupervised machine-learning processes 232. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 232 may not require a response variable; unsupervised processes 232 may be used to find interesting patterns and/or inferences between variables, to determine a degree of correlation between two or more variables, or the like.

Still referring to FIG. 2, machine-learning module 200 may be designed and configured to create a machine-learning model 224 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 2, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 2, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 2, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 2, one or more processes or algorithms described above may be performed by at least a dedicated hardware unit 236. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 236 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 236 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 236 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 3:
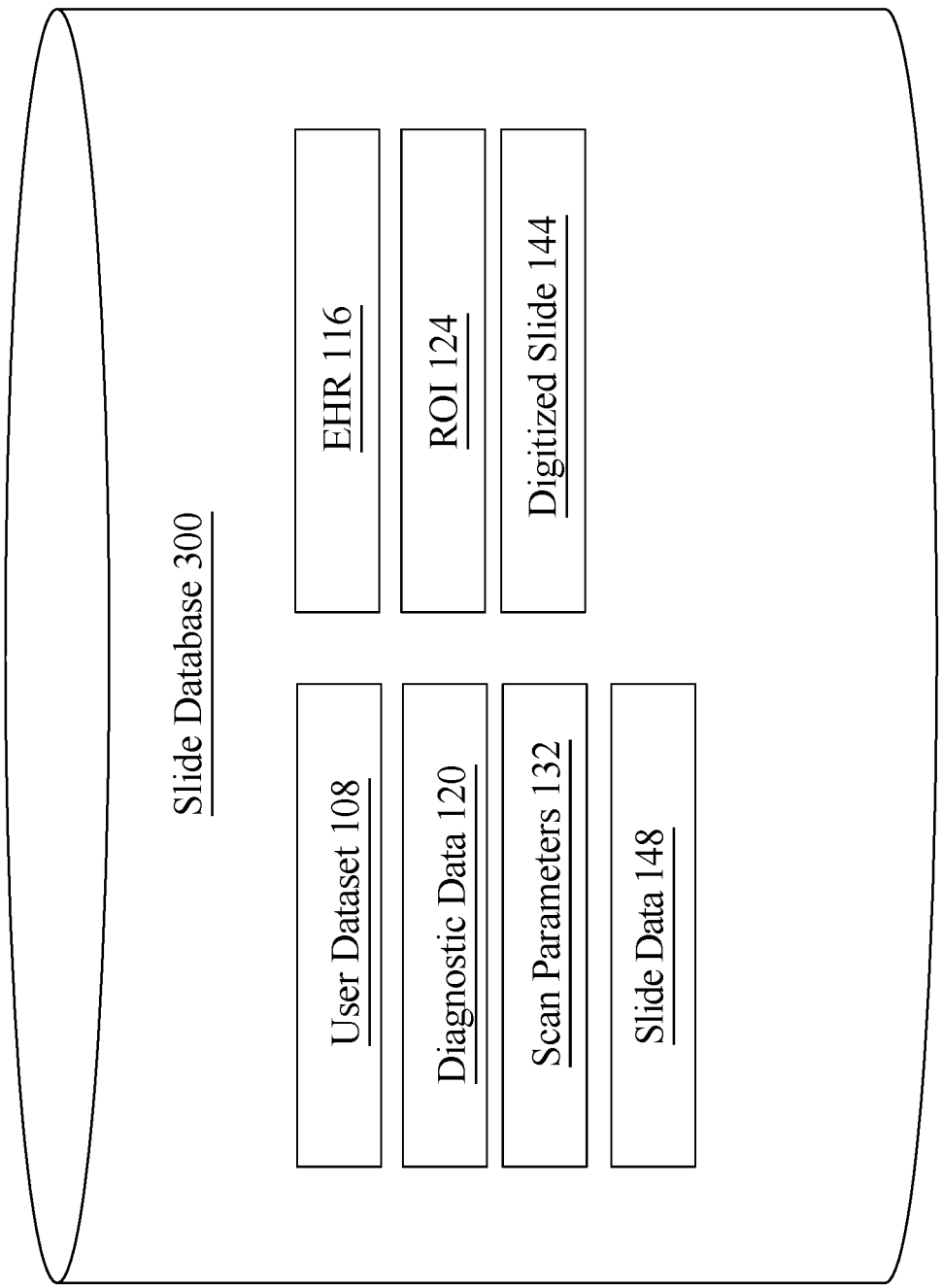
FIG. 3 is a block diagram of an exemplary embodiment of a slide database.

Now referring to FIG. 3, an exemplary slide database 300 is illustrated by way of block diagram. In an embodiment, any past or present versions of any data disclosed herein may be stored within the slide database 300 including but not limited to: user datasets 108, EHRs 116, diagnostic data 120, ROIs 124, scan parameters 132, digitized slides 144, slide data 148, and the like. Processor 104 may be communicatively connected with slide database 300. For example, in some cases, database 300 may be local to processor 104. Alternatively, or additionally, in some cases, database 300 may be remote to processor 104 and communicative with processor 104 by way of one or more networks. Network may include, but not limited to, a cloud network, a mesh network, or the like. By way of example, a "cloud-based" system, as that term is used herein, can refer to a system which includes software and/or data which is stored, managed, and/or processed on a network of remote servers hosted in the "cloud," e.g., via the Internet, rather than on local severs or personal computers. A "mesh network" as used in this disclosure is a local network topology in which the infrastructure processor 104 connects directly, dynamically, and non-hierarchically to as many other computing devices as possible. A "network topology" as used in this disclosure is an arrangement of elements of a communication network, slide database 300 may be implemented, without limitation, as a relational database, a key-value retrieval database such as a NOSQL database, or any other format or structure for use as a database that a person skilled in the art would recognize as suitable upon review of the entirety of this disclosure, slide database 300 may alternatively or additionally be implemented using a distributed data storage protocol and/or data structure, such as a distributed hash table or the like, slide database 300 may include a plurality of data entries and/or records as described above. Data entries in a database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure.

Figure 4:
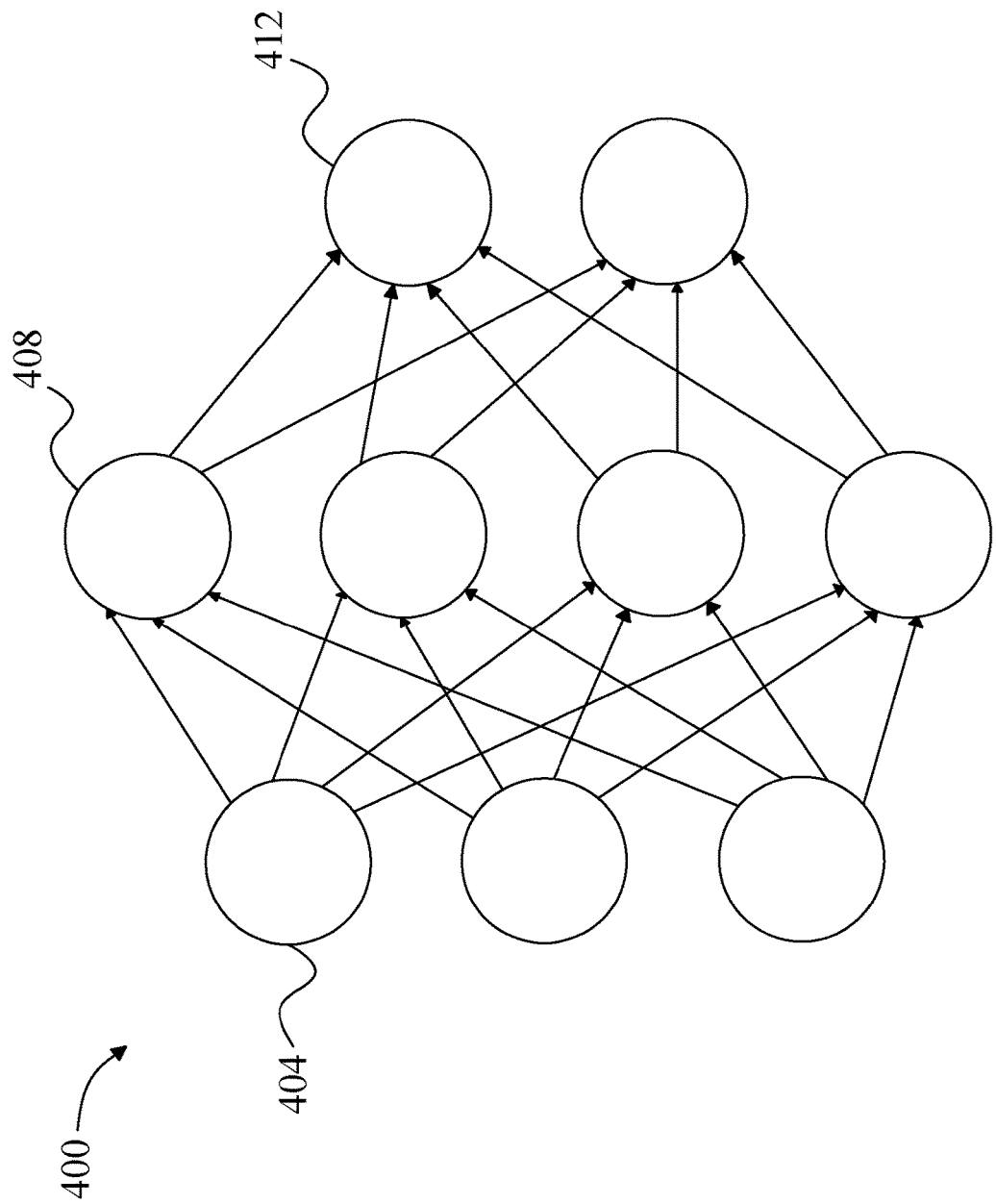
FIG. 4 is a diagram of an exemplary embodiment of a neural network.

Referring now to FIG. 4, an exemplary embodiment of neural network 400 is illustrated. A neural network 400, also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 404, one or more intermediate layers 408, and an output layer of nodes 412. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 5:
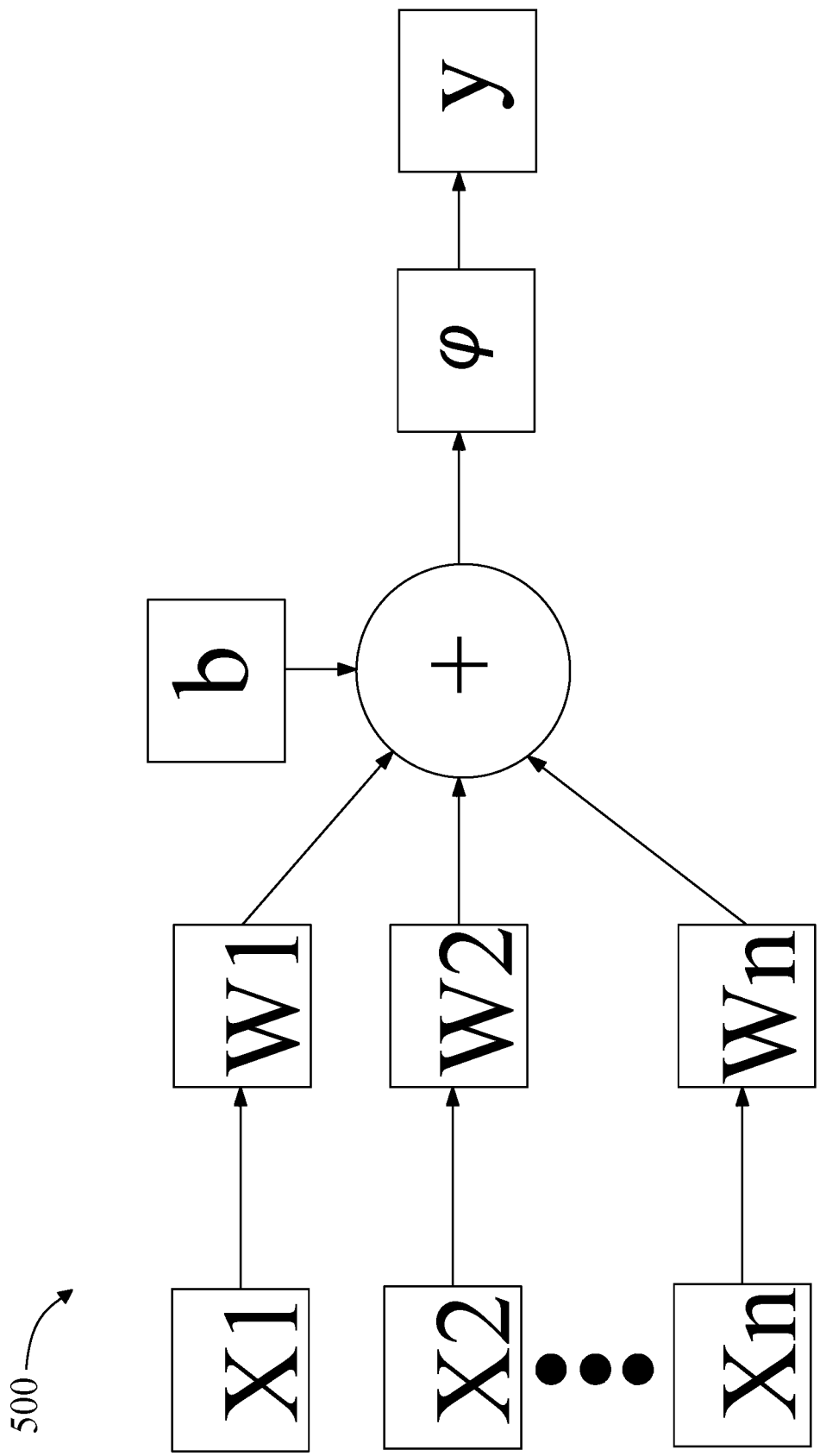
FIG. 5 is a diagram of an exemplary embodiment of a node of a neural network.

Referring now to FIG. 5, an exemplary embodiment of a node of a neural network is illustrated. A node may include, without limitation, a plurality of inputs $x_i$ that may receive numerical values from inputs to a neural network containing the node and/or from other nodes. Node may perform a weighted sum of inputs using weights $w_i$ that are multiplied by respective inputs $x_i$. Additionally, or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figure 6:
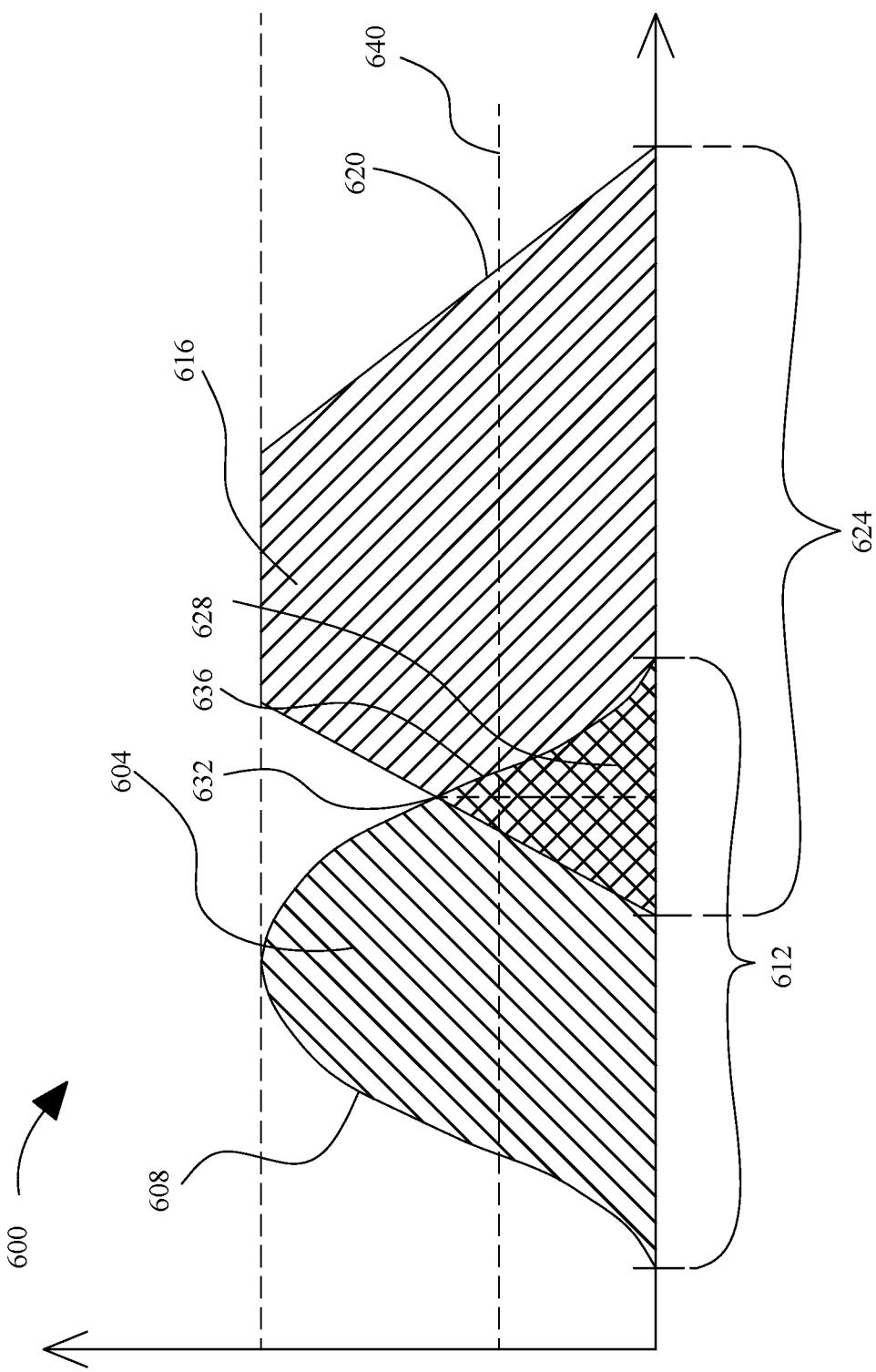
FIG. 6 is an illustration of an exemplary embodiment of fuzzy set comparison.

Now referring to FIG. 6, an exemplary embodiment of fuzzy set comparison 600 is illustrated. In a non-limiting embodiment, the fuzzy set comparison. In a non-limiting embodiment, fuzzy set comparison 600 may be consistent with fuzzy set comparison in FIG. 1. In another non-limiting embodiment the fuzzy set comparison 600 may be consistent with the name/version matching as described herein. For example, and without limitation, the parameters, weights, and/or coefficients of the membership functions may be tuned using any machine-learning methods for the name/version matching as described herein. In another non-limiting embodiment, the fuzzy set may represent a user datasets 108 and an example of ROIs from FIG. 1.

Alternatively, or additionally, and still referring to FIG. 6, fuzzy set comparison 600 may be generated as a function of determining the data compatibility threshold. The compatibility threshold may be determined by a computing device. In some embodiments, a computing device may use a logic comparison program, such as, but not limited to, a fuzzy logic model to determine the compatibility threshold and/or version authenticator. Each such compatibility threshold may be represented as a value for a posting variable representing the compatibility threshold, or in other words a fuzzy set as described above that corresponds to a degree of compatibility and/or allowability as calculated using any statistical, machine-learning, or other method that may occur to a person skilled in the art upon reviewing the entirety of this disclosure. In some embodiments, determining the compatibility threshold and/or version authenticator may include using a linear regression model. A linear regression model may include a machine learning model. A linear regression model may map statistics such as, but not limited to, frequency of the same range of version numbers, and the like, to the compatibility threshold and/or version authenticator. In some embodiments, determining the compatibility threshold of any posting may include using a classification model. A classification model may be configured to input collected data and cluster data to a centroid based on, but not limited to, frequency of appearance of the range of versioning numbers, linguistic indicators of compatibility and/or allowability, and the like. Centroids may include scores assigned to them such that the compatibility threshold may each be assigned a score. In some embodiments, a classification model may include a K-means clustering model. In some embodiments, a classification model may include a particle swarm optimization model. In some embodiments, determining a compatibility threshold may include using a fuzzy inference engine. A fuzzy inference engine may be configured to map one or more compatibility threshold using fuzzy logic. In some embodiments, a plurality of computing devices may be arranged by a logic comparison program into compatibility arrangements. A "compatibility arrangement" as used in this disclosure is any grouping of objects and/or data based on skill level and/or output score. Membership function coefficients and/or constants as described above may be tuned according to classification and/or clustering algorithms. For instance, and without limitation, a clustering algorithm may determine a Gaussian or other distribution of questions about a centroid corresponding to a given compatibility threshold and/or version authenticator, and an iterative or other method may be used to find a membership function, for any membership function type as described above, that minimizes an average error from the statistically determined distribution, such that, for instance, a triangular or Gaussian membership function about a centroid representing a center of the distribution that most closely matches the distribution. Error functions to be minimized, and/or methods of minimization, may be performed without limitation according to any error function and/or error function minimization process and/or method as described in this disclosure.

Still referring to FIG. 6, inference engine may be implemented according to input user datasets 108 and examples of ROIs. For instance, an acceptance variable may represent a first measurable value pertaining to the classification of user datasets 108 to examples of ROIs. Continuing the example, an output variable may represent ROI 124 associated with the user. In an embodiment, user datasets 108 and/or examples of ROIs may be represented by their own fuzzy set. In other embodiments, the classification of the data into ROI 124 may be represented as a function of the intersection two fuzzy sets as shown in FIG. 6, An inference engine may combine rules, such as any semantic versioning, semantic language, version ranges, and the like thereof. The degree to which a given input function membership matches a given rule may be determined by a triangular norm or "T-norm" of the rule or output function with the input function, such as min (a, b), product of a and b, drastic product of a and b, Hamacher product of a and b, or the like, satisfying the rules of commutativity (T(a, b)=T(b, a)), monotonicity: (T(a, b)≤T(c, d) if a≤c and b≤d), (associativity: T(a, T(b, c))=T (T(a, b), c)), and the requirement that the number 1 acts as an identity element. Combinations of rules ("and" or "or" combination of rule membership determinations) may be performed using any T-conorm, as represented by an inverted T symbol or "⊥," such as max (a, b), probabilistic sum of a and b (a+b−a*b), bounded sum, and/or drastic T-conorm; any T-conorm may be used that satisfies the properties of commutativity: ⊥(a, b)=⊥(b, a), monotonicity: ⊥(a, b)≤⊥(c, d) if a≤c and b≤d, associativity: ⊥(a, ⊥(b, c))=⊥(⊥(a, b), c), and identity element of 0. Alternatively, or additionally T-conorm may be approximated by sum, as in a "product-sum" inference engine in which T-norm is product and T-conorm is sum. A final output score or other fuzzy inference output may be determined from an output membership function as described above using any suitable defuzzification process, including without limitation Mean of Max defuzzification, Centroid of Area/Center of Gravity defuzzification, Center Average defuzzification, Bisector of Area defuzzification, or the like. Alternatively, or additionally, output rules may be replaced with functions according to the Takagi-Sugeno-King (TSK) fuzzy model.

A first fuzzy set 604 may be represented, without limitation, according to a first membership function 608 representing a probability that an input falling on a first range of values 612 is a member of the first fuzzy set 604, where the first membership function 608 has values on a range of probabilities such as without limitation the interval [0,1], and an area beneath the first membership function 608 may represent a set of values within first fuzzy set 604. Although first range of values 612 is illustrated for clarity in this exemplary depiction as a range on a single number line or axis, first range of values 612 may be defined on two or more dimensions, representing, for instance, a Cartesian product between a plurality of ranges, curves, axes, spaces, dimensions, or the like. First membership function 608 may include any suitable function mapping first range 612 to a probability interval, including without limitation a triangular function defined by two linear elements such as line segments or planes that intersect at or below the top of the probability interval. As a non-limiting example, triangular membership function may be defined as:

$$(x, a, b, c) = \begin{cases} 0, & \text{for } x > c \text{ and } x < a \\ \frac{x-a}{b-a}, & \text{for } a \leq x < b \\ \frac{c-x}{c-b}, & \text{if } b < x \leq c \end{cases}$$

a trapezoidal membership function may be defined as:

$$y(x, a, b, c, d) = \max\left(\min\left(\frac{x-a}{b-a}, 1, \frac{d-x}{d-c}\right), 0\right)$$

a sigmoidal function may be defined as:

$$y(x, a, c) = \frac{1}{1 - e^{-a(x-c)}}$$

a Gaussian membership function may be defined as:

$$y(x, c, \sigma) = e^{-\frac{1}{2}(\frac{x-c}{\sigma})^2}$$

and a bell membership function may be defined as:

$$y(x, a, b, c,) = \left[1 + \left|\frac{x-c}{a}\right|^{2b}\right]^{-1}$$

Persons skilled in the art, upon reviewing the entirety of this disclosure, will be aware of various alternative or additional membership functions that may be used consistently with this disclosure.

First fuzzy set 604 may represent any value or combination of values as described above, including any user datasets 108 and examples of ROIs. A second fuzzy set 616, which may represent any value which may be represented by first fuzzy set 604, may be defined by a second membership function 620 on a second range 624; second range 624 may be identical and/or overlap with first range 612 and/or may be combined with first range via Cartesian product or the like to generate a mapping permitting evaluation overlap of first fuzzy set 604 and second fuzzy set 616. Where first fuzzy set 604 and second fuzzy set 616 have a region 636 that overlaps, first membership function 608 and second membership function 620 may intersect at a point 632 representing a probability, as defined on probability interval, of a match between first fuzzy set 604 and second fuzzy set 616. Alternatively, or additionally, a single value of first and/or second fuzzy set may be located at a locus 636 on first range 612 and/or second range 624, where a probability of membership may be taken by evaluation of first membership function 608 and/or second membership function 620 at that range point. A probability at 628 and/or 632 may be compared to a threshold 640 to determine whether a positive match is indicated. Threshold 640 may, in a non-limiting example, represent a degree of match between first fuzzy set 604 and second fuzzy set 616, and/or single values therein with each other or with either set, which is sufficient for purposes of the matching process; for instance, the classification into one or more query categories may indicate a sufficient degree of overlap with fuzzy set representing user datasets 108 and examples of ROIs for combination to occur as described above. Each threshold may be established by one or more user inputs. Alternatively, or additionally, each threshold may be tuned by a machine-learning and/or statistical process, for instance and without limitation as described in further detail below.

In an embodiment, a degree of match between fuzzy sets may be used to rank one resource against another. For instance, if both user datasets 108 and examples of ROIs have fuzzy sets, ROI 124 may be generated by having a degree of overlap exceeding a predictive threshold, processor 104 may further rank the two resources by ranking a resource having a higher degree of match more highly than a resource having a lower degree of match. Where multiple fuzzy matches are performed, degrees of match for each respective fuzzy set may be computed and aggregated through, for instance, addition, averaging, or the like, to determine an overall degree of match, which may be used to rank resources; selection between two or more matching resources may be performed by selection of a highest-ranking resource, and/or multiple notifications may be presented to a user in order of ranking.

Figure 7:
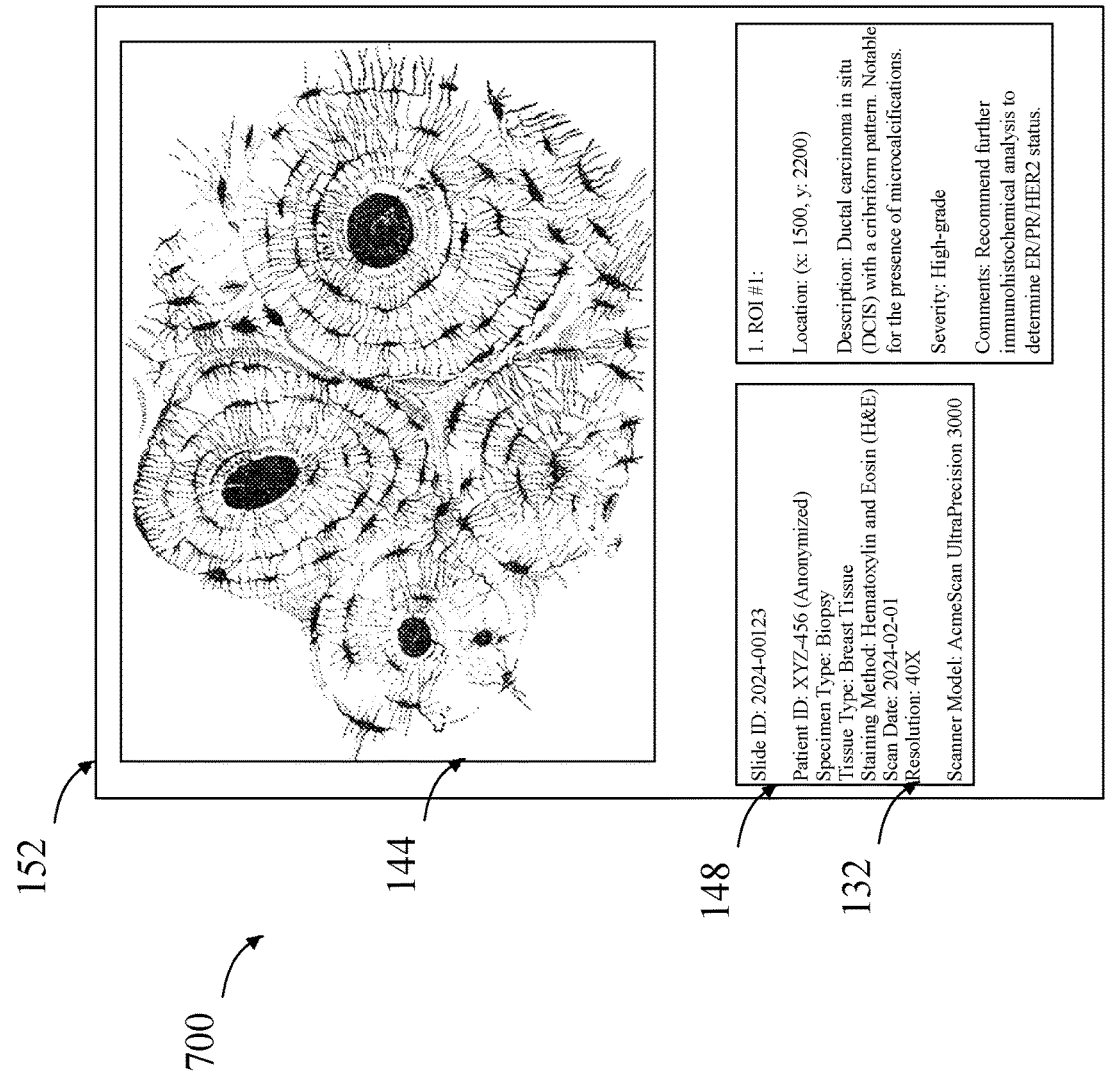
FIG. 7 is an illustration of an exemplary user interface.

Referring now to FIG. 7, is an illustration of an exemplary user interface. User interface 700 is designed to display the digitized slide 148 in a panel that supports various magnification levels, enabling users to explore the slide from a broad overview to the intricate cellular level. This functionality may allow for examining the detailed imagery produced by the advanced single pass scan process. The scanning process itself may be informed by a combination of lab results, such as white blood cells (WBC) count indicating conditions like leucopenia, neutropenia, or lymphopenia, and Electronic Health Records (EHR) data 116, including disease status, drug status, or radiology reports. This data guides the scanner to intelligently focus on suspected pathologies (e.g., TB or breast cancer) and specific regions of interest (ROIs) 124 for microorganisms or tumor detection at high magnification and resolution, without the need for pre-scan ROI 124 identification by clinicians. The user interface 700 may further enhance the user experience by organizing slide data 148 into tabs or sections for Annotations, Metadata, Diagnostic Information, and Reference Links. Users can interact with the digitized slide 144 by clicking on specific ROIs, triggering the sidebar to display relevant annotations and descriptions. This interactive capability is complemented by tools and controls for navigation, including pan, zoom, and rotate, and a search function to quickly locate specific data points within the slide data 148.

Figure 8:
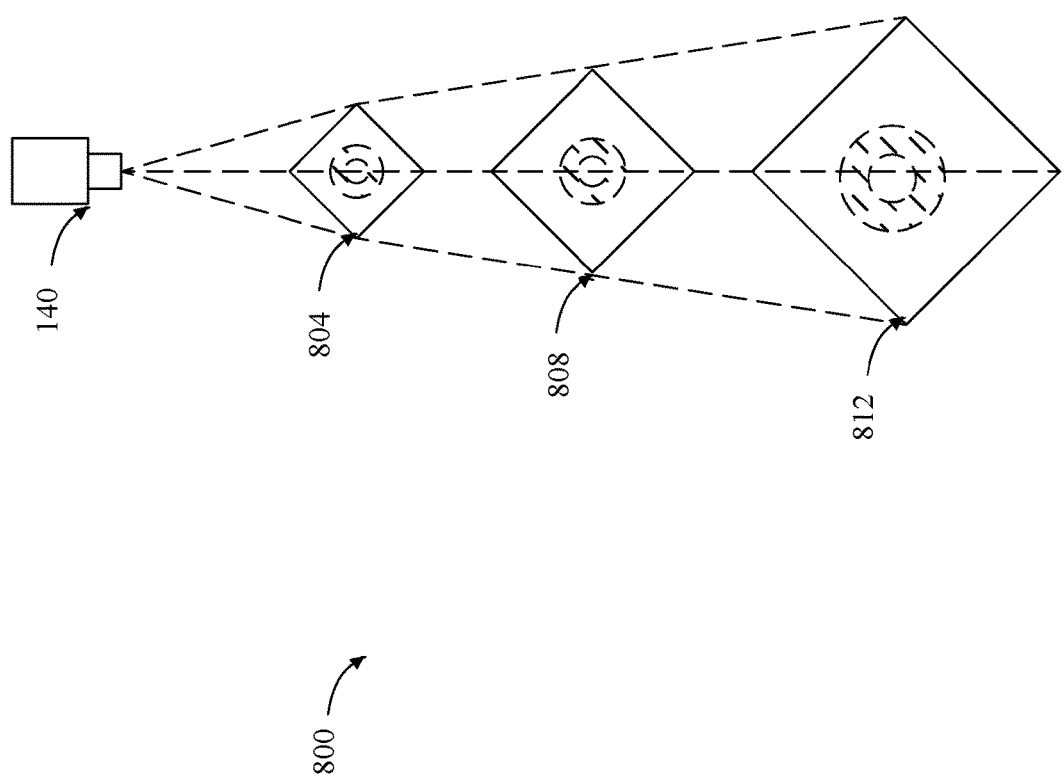
FIG. 8 is a diagram of an exemplary image capture device.

Referring now to FIG. 8, a diagram of an exemplary image capture device 140. FIG. 8 depicts an example digital scan results under different example magnification levels for viewing biological organization, pathological condition, and/or microbe. Magnification and resolution are important features to capture finer details of smaller objects within a digital slide. A first digitized image 804 may depict the pathology slide 112 under a first magnification level. A second digitized image 808 may depict the pathology slide 112 result under a second magnification level. A third digitized image 812 may depict the pathology slide 112 under a third magnification level of the digital scan. Each of the first, second, and third magnification levels may be effective for viewing certain levels of biological organization normal or pathological, as well as microbial organisms. Accordingly, each of the first digitized image 804, the second digitized image 808, and the third digitized image 812 may be a view of an ROI 124 within a digitized slide 144 that is optimized for viewing certain levels of biological organization normal or pathological, as well as microbial organisms. For instance, the first digitized image 804 may be effective for viewing macro structures at a tissue level, including a tissue. The second digitized image 808, with the second magnification level being more fine-grained than the first magnification level, is optimized to view structures at a single-cell level, including a cell. The third digitized image 812, with the third magnification level being more fine-grained than the second magnification level, may be optimized to view organelles within cells. In an example, microbes are best observed at a magnification level of 100 times, which may correspond with a resolution of 1.35 NA.

Figure 9:
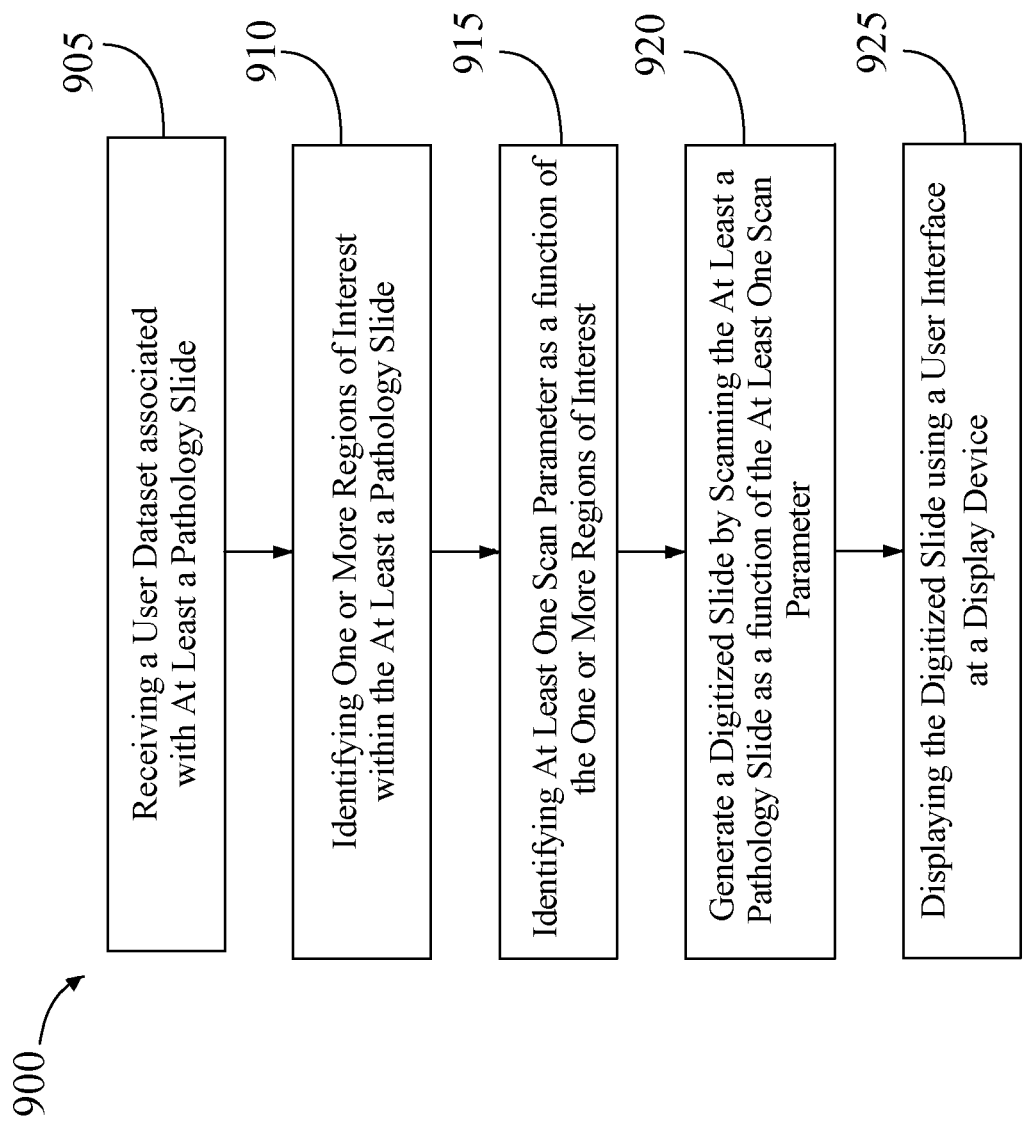
FIG. 9 is a flow diagram of an exemplary method for identifying regions of interest during slide digitization.

Referring now to FIG. 9, a flow diagram of an exemplary method 900 for identifying regions of interest during slide digitization is illustrated. At step 905, method 900 includes receiving, using at least a processor, a user dataset associated with at least a pathology slide. This may be implemented as described and with reference to FIGS. 1-9. In an embodiment, receiving the user dataset may include receiving the user dataset for an electronic health record. In an embodiment, the user dataset may include a plurality of textual data and a plurality of image data associated with the at least a pathology slide.

Still referring to FIG. 9, at step 910, method 900 includes identifying, using the at least a processor, one or more regions of interest within at least a pathology slide as a function of the user dataset. This may be implemented as described and with reference to FIGS. 1-9. In an embodiment, the method may include generating diagnostic data as a function of the user dataset. The method may also include identifying the one or more regions of interest as a function of the diagnostic data. In another embodiment, identifying the one or more regions of interest may include iteratively training an identification machine learning model using identification training data, wherein the identification training data comprises a plurality of user datasets as inputs correlated to examples of regions of interest as outputs. The method may also include identifying one or more regions of interest using a trained identification machine learning model. In some cases, identification training data may include a plurality of associations between image data and textual data.

Still referring to FIG. 9, at step 915, method 900 includes identifying, using the at least a processor, at least one scan parameter as a function of the one or more regions of interest. This may be implemented as described and with reference to FIGS. 1-9. In an embodiment, the at least one scan parameter may include a magnification level and/or focus depth.

Still referring to FIG. 9, at step 920, method 900 includes generating, using the at least a processor, a digitized slide by scanning the at least a pathology slide as a function the at least one scan parameter. This may be implemented as described and with reference to FIGS. 1-9. In an embodiment, the method may include generating, using the at least a processor, a plurality of slide data as a function of the digitized slide and the user dataset. The method may also include attaching, using the at least a processor, the plurality of slide data to the digitized slide as metadata. In another embodiment, scanning the at least a pathology slide comprises scanning the at least a pathology slide in a single pass.

Still referring to FIG. 9, at step 925, method 900 includes displaying the digitized slide using a user interface at a display device. This may be implemented as described and with reference to FIGS. 1-9.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 10:
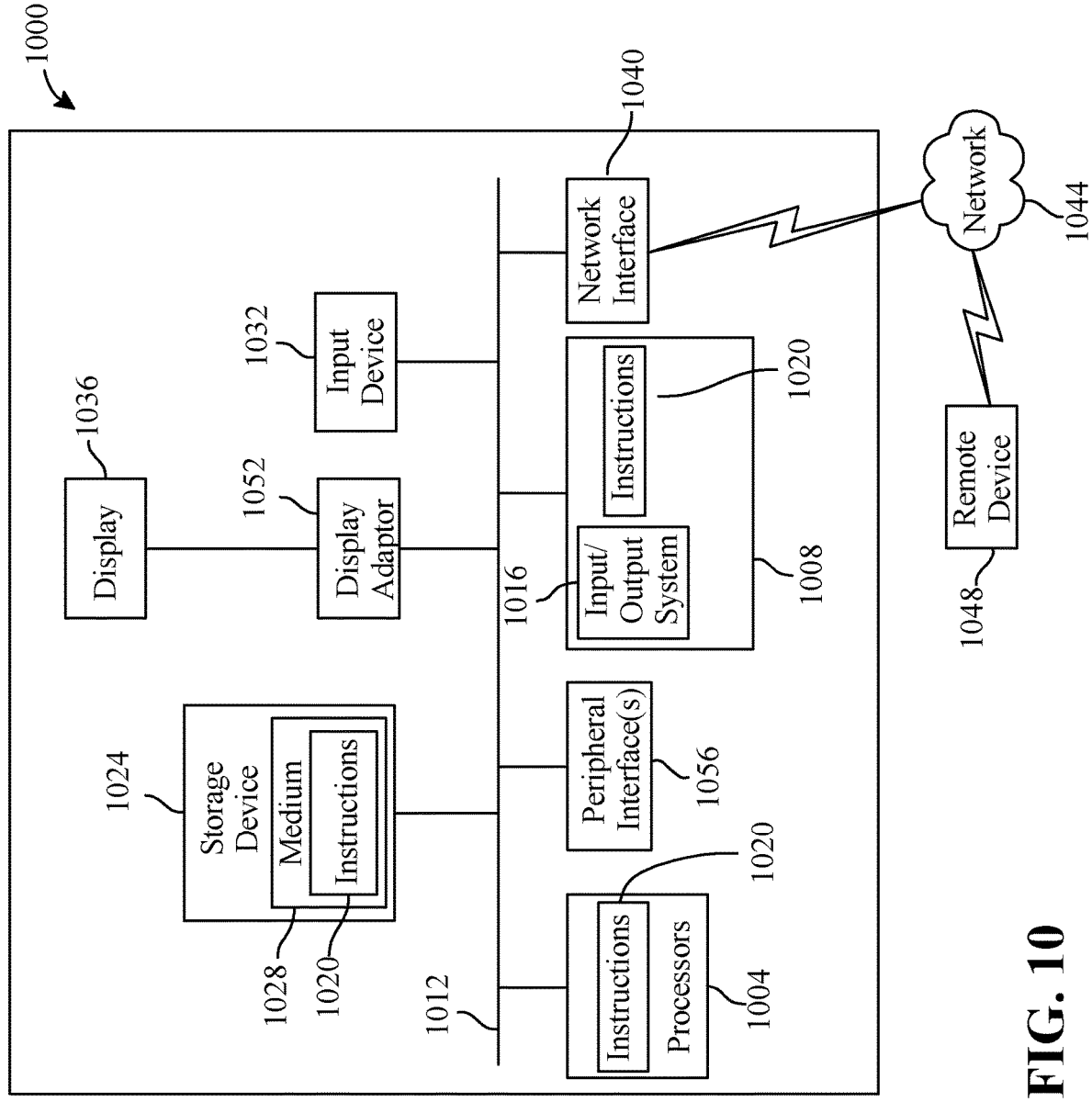
FIG. 10 is a block diagram of a computing system that can be used to implement any one or more of the methodologies disclosed herein and any one or more portions thereof.

FIG. 10 shows a diagrammatic representation of one embodiment of a computing device in the exemplary form of a computer system 1000 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1000 includes a processor 1004 and a memory 1008 that communicate with each other, and with other components, via a bus 1012. Bus 1012 may include any of several types of bus structures including, but not limited to, a memory bus, a memory controller, a peripheral bus, a local bus, and any combinations thereof, using any of a variety of bus architectures.

Processor 1004 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 1004 may be organized according to Von Neumann and/or Harvard architecture as a non-limiting example. Processor 1004 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 1008 may include various components (e.g., machine-readable media) including, but not limited to, a random-access memory component, a read only component, and any combinations thereof. In one example, a basic input/output system 1016 (BIOS), including basic routines that help to transfer information between elements within computer system 900, such as during start-up, may be stored in memory 908. Memory 908 may also include (e.g., stored on one or more machine-readable media) instructions (e.g., software) 1020 embodying any one or more of the aspects and/or methodologies of the present disclosure. In another example, memory 1008 may further include any number of program modules including, but not limited to, an operating system, one or more application programs, other program modules, program data, and any combinations thereof.

Computer system 1000 may also include a storage device 1024. Examples of a storage device (e.g., storage device 1024) include, but are not limited to, a hard disk drive, a magnetic disk drive, an optical disc drive in combination with an optical medium, a solid-state memory device, and any combinations thereof. Storage device 1024 may be connected to bus 1012 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1024 (or one or more components thereof) may be removably interfaced with computer system 1000 (e.g., via an external port connector (not shown)). Particularly, storage device 1024 and an associated machine-readable medium 1028 may provide nonvolatile and/or volatile storage of machine-readable instructions, data structures, program modules, and/or other data for computer system 1000. In one example, software 1020 may reside, completely or partially, within machine-readable medium 1028. In another example, software 1020 may reside, completely or partially, within processor 1004.

Computer system 1000 may also include an input device 1032. In one example, a user of computer system 1000 may enter commands and/or other information into computer system 1000 via input device 1032. Examples of an input device 1032 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1032 may be interfaced to bus 1012 via any of a variety of interfaces (not shown) including, but not limited to, a serial interface, a parallel interface, a game port, a USB interface, a FIREWIRE interface, a direct interface to bus 1012, and any combinations thereof. Input device 1032 may include a touch screen interface that may be a part of or separate from display 1036, discussed further below. Input device 1032 may be utilized as a user selection device for selecting one or more graphical representations in a graphical interface as described above.

A user may also input commands and/or other information to computer system 1000 via storage device 1024 (e.g., a removable disk drive, a flash drive, etc.) and/or network interface device 1040. A network interface device, such as network interface device 1040, may be utilized for connecting computer system 1000 to one or more of a variety of networks, such as network 1044, and one or more remote devices 1048 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1044, may employ a wired and/or a wireless mode of communication. In general, any network topology may be used. Information (e.g., data, software 1020, etc.) may be communicated to and/or from computer system 1000 via network interface device 1040.

Computer system 1000 may further include a video display adapter 1052 for communicating a displayable image to a display device, such as display device 1036. Examples of a display device include, but are not limited to, a liquid crystal display (LCD), a cathode ray tube (CRT), a plasma display, a light emitting diode (LED) display, and any combinations thereof. Display adapter 1052 and display device 1036 may be utilized in combination with processor 1004 to provide graphical representations of aspects of the present disclosure. In addition to a display device, computer system 1000 may include one or more other peripheral output devices including, but not limited to, an audio speaker, a printer, and any combinations thereof. Such peripheral output devices may be connected to bus 1012 via a peripheral interface 1056. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions, and additions may be made to that which is specifically disclosed herein without departing from the spirit and scope of the present invention.

What is claimed is:

1. An apparatus for identifying regions of interest during slide digitization, wherein the apparatus comprises:
   at least a processor; and
   a memory communicatively connected to the at least a processor, wherein the memory comprises instructions configuring the at least a processor to:
   receive identification data as a function of a user dataset associated with at least a pathology slide;
   identify one or more regions of interest within the at least a pathology slide as a function of the user dataset;
   identify at least one scan parameter as a function of the one or more regions of interest;
   train a machine learning model iteratively with identification training data, wherein the identification training data correlates a plurality of pathology slides and the user dataset to a plurality of regions of interest;
   calculate an accuracy score for the machine learning model, wherein the accuracy score identifies regions of interest within a plurality of pathology slides;
   modify the pathology slide by the identification training data as a function of user feedback and accuracy score;
   retrain the machine learning model by iteratively adding outputs of the machine learning model to the plurality of pathology slides and the user data set;
   generate a digitized slide by scanning the at least a modified pathology slide as a function of the at least one scan parameter;
   process images from the modified pathology slide, wherein processing the images comprises enhancing at least a region of interest by performing a color space conversation operation; and
   display the digitized slide using a user interface at a display device.

2. The apparatus of claim 1, wherein receiving the user dataset comprises receiving the user dataset for an electronic health record.

3. The apparatus of claim 1, wherein the memory comprises instructions configuring the at least a processor to:
   generate diagnostic data as a function of the user dataset; and
   identify the one or more regions of interest as a function of the diagnostic data.

4. The apparatus of claim 1, wherein the memory comprises instructions configuring the at least a processor to generate a plurality of slide data as a function of the digitized slide and the user dataset.

5. The apparatus of claim 4, wherein the memory comprises instructions configuring the at least a processor to attach the plurality of slide data to the digitized slide as metadata.

6. The apparatus of claim 1, wherein the user dataset comprises:
a plurality of textual data associated with the at least a pathology slide; and
a plurality of image data associated with the at least a pathology slide.

7. The apparatus of claim 1, wherein the at least one scan parameter comprises a magnification level.

8. The apparatus of claim 1, wherein the at least one scan parameter comprises a focus depth.

9. The apparatus of claim 1, wherein scanning the at least a pathology slide comprises scanning the at least a pathology slide in a single pass.

10. A method for identifying regions of interest during slide digitization, wherein the method comprises:
receiving, using at least a processor, a user dataset associated with at least a pathology slide;
identifying, using the at least a processor, one or more regions of interest within the at least a pathology slide as a function of the user dataset;
identifying, using the at least a processor, at least one scan parameter as a function of the one or more regions of interest;
training a machine learning model iteratively with identification training data, wherein the identification training data correlates a plurality of pathology slides and the user dataset to a plurality of regions of interest;
calculating an accuracy score for the machine learning model, wherein the accuracy score identifies regions of interest within a plurality of pathology slides;
modify the pathology slide by the identification training data as a function of user feedback and accuracy score;
retrain the machine learning model by iteratively adding outputs of the machine learning model to the plurality of pathology slides and the user data set;
generate a digitized slide by scanning the at least a modified pathology slide as a function of the at least one scan parameter;
process images from the modified pathology slide, wherein processing the images comprises enhancing at least a region of interest by performing a color space conversation operation; and
displaying, using a user interface at a display device, the digitized slide.

11. The method of claim 10, wherein receiving the user dataset comprises receiving the user dataset for an electronic health record.

12. The method of claim 10, further comprising:
generating, using the at least a processor, diagnostic data as a function of the user dataset; and
identifying, using the at least a processor, the one or more regions of interest as a function of the diagnostic data.

13. The method of claim 10, further comprising:
generating, using the at least a processor, a plurality of slide data as a function of the digitized slide and the user dataset.

14. The method of claim 13, further comprising:
attaching, using the at least a processor, the plurality of slide data to the digitized slide as metadata.

15. The method of claim 10, wherein the user dataset comprises:
a plurality of textual data associated with the at least a pathology slide; and
a plurality of image data associated with the at least a pathology slide.

16. The method of claim 10, wherein the at least one scan parameter comprises a magnification level.

17. The method of claim 10, wherein the at least one scan parameter comprises a focus depth.

18. The method of claim 10, wherein scanning the at least a pathology slide comprises scanning the at least a pathology slide in a single pass.

* * * * *